United States Patent
Nakano et al.

(10) Patent No.: US 6,344,590 B1
(45) Date of Patent: *Feb. 5, 2002

(54) ADAMANTANEMETHANOL DERIVATIVES AND PRODUCTION PROCESSES THEREOF

(75) Inventors: Tatsuya Nakano, Hyogo; Hiroshi Shimojitosyo, Osaka, both of (JP)

(73) Assignee: Daicel Chemical Industries, Ltd., Sakai (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/468,326

(22) Filed: Dec. 21, 1999

Related U.S. Application Data

(63) Continuation of application No. PCT/JP99/02110, filed on Apr. 21, 1999.

(30) Foreign Application Priority Data

| Apr. 21, 1998 | (JP) | 10-128296 |
| Oct. 7, 1998 | (JP) | 10-285632 |
| Mar. 17, 1999 | (JP) | 11-072669 |

(51) Int. Cl.$^7$ ............................................. C07C 43/30
(52) U.S. Cl. ...................... 568/591; 556/449; 558/429; 560/117; 562/449; 568/373; 568/665; 568/818
(58) Field of Search .................. 568/818, 665, 568/373, 591; 560/117; 562/449; 558/429; 556/449

(56) References Cited

U.S. PATENT DOCUMENTS 4,440,692 A * 4/1984 Kalbacher .................. 568/818

FOREIGN PATENT DOCUMENTS

JP 64-25753 * 1/1989

OTHER PUBLICATIONS

Svishchuk, Chem. Abstr. vol. 96(15), p. 660, Section 122277y, 1982.*

Dua, J. Chem. Soc., Perkin Trans. 2, pp. 1443–1448, Jun. 1998.*

Kraus, J. Org. Chem., vol. 69, pp. 922–923, 1994.*

Heagy, Michael D. et al, "Preparation and 13C NMR Spectroscopic Study of Disubstituted Adamantane–1–3–dimethyldiyl Dications", J. Org. Chem., 1995, vol. 60, No. 22, p. 7351–7354.

Kovalev, V.V. et al, "Reaction of 1–adamantanol with α–olefins in trifluoroacetic acid", Zh. Org. Khim., 1981, vol. 17, No. 1, p. 109–116. (No transtation).

Lomas, John S. et al, "Structure and isotope effects upon the thermal decomposition of carbamates of highly congested tertiary alcohols," J. Chem. Soc. Perkin Trans. 2, 1982, No. 2, p. 221–226.

Olah, George A. et al, "Stable carbocations. Part 235. Solvolytic and stable ion studies of 1,1'–diadamanthylmethyl cations," J. Org. Chem., 1982, vol. 47, No. 6, p. 1040–1047.

Lomas, John S. et al., "Acid–catalyzed dehydration and acetolysis of tertiary methyl–and tert–butylcarbinols. Empirical force field treatment of tert–butyl/methyl reactivity ratios in solvolysis reactions of alcohols and p–nitrobenzoates," J. Org. Chem. , 1979, vol. 44, No. 10, p. 1647–1654.

Edwards, Gray J. et al., "Anodic oxidation of substituted adamantanes," J. Chem. S., Perkin Trans. 2, 1997, No. 4, p. 505–510.

* cited by examiner

Primary Examiner—Michael L. Shippen
(74) Attorney, Agent, or Firm—Oblon, Spivak, McClelland, Maier & Neustadt, P.C.

(57) ABSTRACT

An adamantanemethanol derivative of the invention is represented by the following formula (1), wherein $R^a$ is a hydrogen atom or a hydrocarbon group; $R^b$ is a hydrocarbon group having a carbon atom, to which carbon atom at least one hydrogen atom is bonded, at a bonding site with the adjacent carbon atom; $R^c$, $R^d$ and $R^e$ are each a hydrogen atom, a hydroxyl group which may be protected by a protective group or the like; provided that a hydroxyl group protected by a protective group or the like is bonded to at least one carbon atom constituting the adamantane skeleton when $R^a$ is a hydrogen atom or a methyl group and $R^b$ is a methyl group; and at least one substituent, in addition to the HO—C($R^a$)($R^b$)— group indicated in the formula (1), is bonded to the adamantane ring when one of $R^a$ and $R^b$ is a methyl group and the other is an ethyl group.

(1)

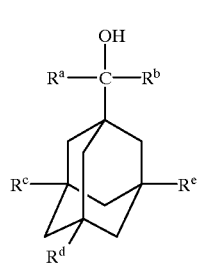

13 Claims, No Drawings

ADAMANTANEMETHANOL DERIVATIVES AND PRODUCTION PROCESSES THEREOF

This application is a Continuation of international PCT application No. PCT/JP99/02110, Filed on Apr. 21, 1999.

TECHNICAL FIELD

The present invention relates to novel adamantanemethanol derivatives which are useful as, for example, monomers or their materials for photosensitive resins and other functional polymers and to production processes thereof.

BACKGROUND ART

Alicyclic compounds each having a hydroxymethyl group have been used as monomers or their materials for resist resins, and pharmaceutical intermediates, and have received attention in recent years.

However, adamantanemethanol derivatives having a hydrocarbon group, which hydrocarbon group is bonded to a carbon atom adjacent to a hydroxyl group and has a methine carbon atom at a bonding site with the carbon atom, and adamantanemethanol derivatives each having a hydroxyl group protected by a protective group on its adamantane ring, and production processes thereof have not yet been known.

DISCLOSURE OF INVENTION

Accordingly, it is an object of the present invention to provide adamantanemethanol derivatives each having a hydrocarbon group, which hydrocarbon group is bonded to a carbon atom adjacent to a hydroxyl group and has a methine carbon atom at a bonding site with the carbon atom, adamantanemethanol derivatives each having a hydroxyl group protected by a protective group on the adamantane ring, and other novel adamantanemethanol derivatives, and production processes thereof.

After intensive investigations to achieve the above object, the present inventors found that novel adamantanemethanol derivatives each having a specific substituent introduced into a carbon atom adjacent to a hydroxyl group (carbon atom at the α-position) can be obtained by allowing organometallic compounds on 1-acyladamantane derivatives and/or 1-adamantanecarboxylic acid derivatives. The present invention has been accomplished based on the above finding.

To be more specific, the invention provides, in an aspect, an adamantanemethanol derivative represented by the following formula (1):

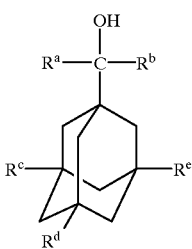
(1)

[wherein $R^a$ is a hydrogen atom or a hydrocarbon group; $R^b$ is a hydrocarbon group having a carbon atom, to which carbon atom at least one hydrogen atom is bonded, at a bonding site with the adjacent carbon atom; $R^c$, $R_d$ and $R^e$ are each, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, or a group represented by the following formula (2):

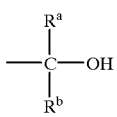
(2)

(wherein $R^a$ and $R^b$ have the same meanings as defined above); where the other carbon atoms of carbon atoms constituting the adamantane skeleton than those at the bridgehead positions may have a substituent; provided that (a) when $R^a$ is a hydrogen atom or a methyl group and $R^b$ is a methyl group, a hydroxyl group which is protected by a protective group, a hydroxymethyl group which may be protected by a protective group, an amino group which may be protected by a protective group, a carboxyl group which may be protected by a protective group, a nitro group, an acyl group or a group represented by the formula (2) is bonded to at least one carbon atom constituting the adamantane skeleton; and (b) when one of $R^a$ and $R^b$ is a methyl group and the other is an ethyl group, at least one substituent, in addition to the HO—C($R^a$)($R^b$)— group indicated in the formula (1), is bonded to the adamantane ring].

In the formula (1), $R^b$ may be a hydrocarbon group having a methine carbon atom at a bonding site with the adjacent carbon atom. Separately, $R^a$ and $R^b$ may be, identical to or different from each other, a $C_2$–$C_{10}$ alkyl group or a 3- to 8-membered cycloalkyl group, or $R^a$ and $R^b$ may be the same hydrocarbon group. Furthermore, a hydroxyl group protected by a protective group may be bonded to at least one carbon atom constituting the adamantane skeleton.

The compounds represented by the formula (1) include adamantanemethanol derivatives represented by the following formula (1c):

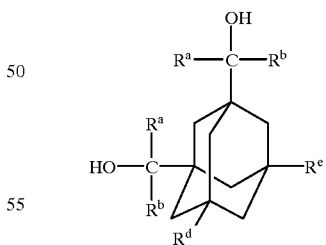
(1c)

[wherein $R^a$ is a hydrogen atom or a hydrocarbon group; $R^b$ is a hydrocarbon group having a carbon atom, to which carbon atom at least one hydrogen atom is bonded, at a bonding site with the adjacent carbon atom; $R^d$ and $R^e$ are each, identical to or different from each other, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, or a group represented by the following formula (2):

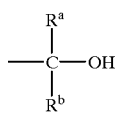

(2)

(wherein $R^a$ and $R^b$ have the same meanings as defined above); provided that $R^d$ and $R^e$ are not concurrently hydrogen atoms]. In these adamantanemethanol derivatives, $R^d$ may be a hydroxyl group which may be protected by a protective group.

The invention provides, in another aspect, a process for the production of an adamantanemethanol derivative (hereinafter may be referred to as "production process 1"), the process comprising the step of reacting an adamantane derivative represented by the following formula (3):

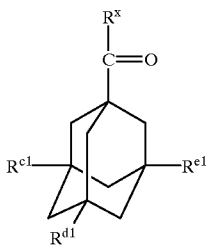

(3)

with an organometallic compound represented by the following formula (4):

$$R^y—M \quad (4)$$

to give a compound represented by the formula (1).

In the above formulae (3) and (4), $R^x$ and $R^y$ each represent the aforementioned $R^a$ or $R^b$, and $R^y$ is $R^b$ when $R^x$ is $R^a$, and $R^y$ is $R^a$ when $R^x$ is $R^b$; $R^{c1}$, $R^{d1}$ and $R^{e1}$ are each, identical to or different from one another, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group or an acyl group; where the other carbon atoms of carbon atoms constituting the adamantane skeleton than those at the bridgehead positions may have a substituent; provided that (a) when both $R^x$ and $R^y$ are methyl groups, or one is a hydrogen atom and the other is a methyl group, a hydroxyl group which is protected by a protective group, a hydroxymethyl group which may be protected by a protective group, an amino group which may be protected by a protective group, a carboxyl group which may be protected by a protective group, a nitro group, an acyl group, or a group represented by the formula (2) is bonded to at least one carbon atom constituting the adamantane skeleton; and (b) when one of $R^x$ and $R^y$ is a methyl group and the other is an ethyl group, at least one substituent, in addition to the $R^xC(=O)—$ group indicated in the formula (3), is bonded to the adamantane ring; M is a metal atom which may have a ligand, or a group represented by the following formula (5):

$$—MgY \quad (5)$$

(wherein Y is a halogen atom).

In a further aspect, the invention provides a process for the production of an adamantanemethanol derivative (hereinafter may be referred to as "production process 2"), the process comprising the steps of: subjecting a hydroxyadamantanecarboxylic acid derivative represented by the following formula (12a):

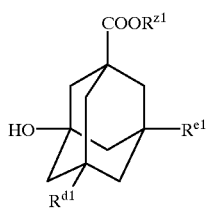

(12a)

(wherein $R^{z1}$ is a hydrogen atom or a hydrocarbon group which may have a substituent; $R^{d1}$ and $R^{e1}$ are each, identical to or different from each other, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group or an acyl group; where the other carbon atoms of carbon atoms constituting the adamantane skeleton than those at the bridgehead positions may have a substituent) to a reaction for the introduction of a protective group to give a compound represented by the following formula (12b):

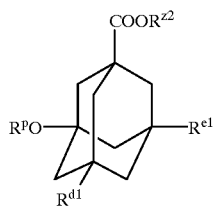

(12b)

(wherein $R^{z2}$ is a hydrogen atom or a hydrocarbon group which may have a substituent; $R^p$ is a protective group for hydroxyl group; $R^{d1}$ and $R^{e1}$ have the same meanings as defined above; where the other carbon atoms of carbon atoms constituting the adamantane skeleton than those at the bridgehead positions may have a substituent), and reacting the compound with an organometallic compound represented by the following formula (4a):

$$R^{a1}—M \quad (4a)$$

[wherein $R^{a1}$ is a hydrocarbon group having a carbon atom, to which carbon atom at least one hydrogen atom is bonded, at a bonding site with the adjacent M; and M is a metal atom which may have a ligand, or a group represented by the following formula (5):

$$—MgY \quad (5)$$

(wherein Y is a halogen atom)] to give a compound represented by the following formula (1b):

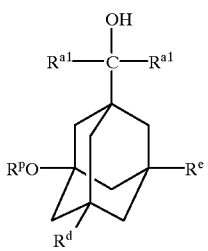

(1b)

[wherein $R^{a1}$ and $R^p$ have the same meanings as defined above; $R^d$ and $R^e$ are each, identical to or different from each other, a hydrogen atom, a halogen atom, an alkyl group, a hydroxyl group which may be protected by a protective group, a hydroxymethyl group which may be protected by a protective group, an amino group which may be protected by a protective group, a carboxyl group which may be protected by a protective group, a nitro group, an acyl group, or a group represented by the following formula (2a):

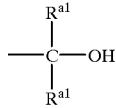

(2a)

(wherein $R^{a1}$ has the same meaning as defined above): where the other carbon atoms of carbon atoms constituting the adamantane skeleton than those at the bridgehead positions may have a substituent].

In the present description, the term "group protected by a protective group" means a group which can be derived from a group to be protected (a free functional group) and contains a primary moiety of the group to be protected.

BEST MODE FOR CARRYING OUT THE INVENTION

Adamantanemethanol Derivatives

In the formula (1), hydrocarbon groups in $R^a$ include, but are not limited to, methyl, ethyl, propyl, isopropyl, butyl, isobutyl, s-butyl, t-butyl, pentyl, isopentyl, 1-methylbutyl, 1-ethylpropyl, hexyl, isohexyl, 1-methylpentyl, 1-ethylbutyl, 1-methylhexyl, 1-ethylpentyl, 1-propylbutyl, octyl, isooctyl, 1-methylheptyl, 1-ethylhexyl, 1-propylpenyl, nonyl, isononyl, 1-methyloctyl, decyl, 1-methylnonyl, tetradecyl, hexadecyl, octadecyl, allyl, propynyl, and other straight- or branched-chain aliphatic hydrocarbon groups (alkyl groups, alkenyl groups and alkynyl groups) each having about 1 to 20 (preferably 1 to 10, and typically 1 to 6) carbon atoms; cyclopropyl, cyclobutyl, cyclopentyl, cyclohexyl, cyclohexenyl, cyclooctyl, and other alicyclic hydrocarbon groups (cycloalkyl groups and cycloalkenyl groups) each having about 3 to 8 carbon atoms; and phenyl, naphthyl, and other aromatic hydrocarbon groups (aryl groups) each having about 6 to 14 carbon atoms. These hydrocarbon groups may have a substituent.

Preferable $R^a$ includes, for example, a hydrogen atom alkyl groups each having about 1 to 10 (particularly 1 to 6) carbon atoms and 3- to 8-membered cycloalkyl groups. Among them, typically preferred $R^a$ is, for instance, methyl, ethyl, propyl, butyl, pentyl, and other alkyl groups each having about 1 to 5 carbon atoms, and hydrocarbon groups having a methine carbon atom at a bonding site with the adjacent carbon atom (e.g., isopropyl, s-butyl, 1-methylbutyl, 1-ethylpropyl, and other alkyl groups having a methine carbon atom at a bonding site with the adjacent carbon atom and having about 3 to 10 (especially 3 to 6) carbon atoms; cyclopropyl, cyclobutyl, cyclopentyl, cyclohexyl, and other 3- to 8-membered cycloalkyl groups). $R^a$ is a hydrogen atom, or an alkyl group having about 1 to 4 carbon atom, in particular a methyl group or an ethyl group in many cases.

The "hydrocarbon group having a carbon atom, to which carbon atom at least one hydrogen atom is bonded, at a bonding site with the adjacent carbon atom" in $R^b$ includes hydrocarbon groups each having a methine carbon atom or a methylene carbon atom at a bonding site with the adjacent carbon atom, and a methyl group. Such hydrocarbon groups having a methine carbon atom at a bonding site with the adjacent carbon atom include groups represented by the following formula (6):

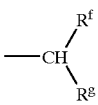

(6)

(wherein $R^f$ and $R^g$ are each, identical to or different from each other, a hydrocarbon group, where $R^f$ and $R^g$ may form a ring with the adjacent methine carbon atom).

As hydrocarbon groups in $R^f$ and $R^g$, there may be mentioned similar groups as in the hydrocarbon groups in $R^a$. Preferred hydrocarbon groups as $R^f$ and $R^g$ are, for example, alkyl groups each having about 1 to 9 (especially 1 to 4) carbon atoms, 3- to 8-membered cycloalkyl groups, and aromatic hydrocarbon groups each having about 6 to 14 carbon atoms, among which methyl, ethyl, propyl, butyl and other alkyl groups each having 1 to 4 carbon atoms are typically preferred.

Rings formed by $R^f$ and $R^g$ together with the adjacent methine carbon atom include, but are not limited to, cyclopropyl, cyclobutyl, cyclopentyl, cyclohexyl, cyclooctyl and other 3- to 8-membered cycloalkyl groups; and cyclopentenyl, cyclohexenyl and other cycloalkenyl groups each having 3 to 8 carbon atoms or members.

Typical examples of the "hydrocarbon groups having a methine carbon atom at a bonding site with the adjacent carbon atom" in $R^b$ include, but are not limited to, isopropyl, s-butyl, 1-methylbutyl, 1-ethylpropyl, 1-methylpentyl, 1-ethylbutyl, 1-methylhexyl, 1-ethylpentyl, 1-propylbutyl, 1-methylheptyl, 1-ethylhexyl, 1-propylpentyl, 1-methyloctyl, 1-methylnonyl, and other alkyl groups having a methine carbon atom at a bonding site with the adjacent carbon atom and having about 3 to 10 (preferably 3 to 6, and particularly 3 or 4) carbon atoms; and the aforementioned 3- to 8-membered cycloalkyl groups.

Examples of the "hydrocarbon groups having a methylene carbon atom at a bonding site with the adjacent carbon atom" in $R^b$ include ethyl, propyl, butyl, isobutyl, pentyl, isopentyl, hexyl, isohexyl, octyl, isooctyl, pentenyl, hexenyl, hexynyl, and other alkyl groups, alkenyl groups or alkynyl groups (especially alkyl groups) each having about 2 to 10 (e.g., 3 to 10) carbon atoms.

Halogen atoms in the above substituents $R^c$, $R^d$ and $R^e$ include, for instance, fluorine, chlorine and bromine atoms. The alkyl groups include methyl, ethyl, propyl, isopropyl, butyl, isobutyl, s-butyl, t-butyl, pentyl, hexyl, octyl, decyl, and other alkyl groups having about 1 to 10 carbon atoms, preferably about 1 to 6 carbon atoms and more preferably about 1 to 4 carbon atoms. The typically preferred alkyl groups are methyl group and ethyl group, particularly methyl group.

Protective groups for hydroxyl group and hydroxymethyl group in $R^c$, $R^d$ and $R^e$ include conventional protective groups. Such protective groups include, but are not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl, 2,6-dichlorobenzyl, 3-bromobenzyl, 2-nitrobenzyl, and triphenylmethyl groups); substituted methyl groups (e.g., methoxymethyl, methylthiomethyl, benzyloxymethyl, t-butoxymethyl, 2-methoxyethoxymethyl, 2,2,2-trichloroethoxymethyl, bis(2-chloroethoxy)methyl, and 2-(trimethylsilyl)ethoxymethyl groups), substituted ethyl groups (e.g., 1-ethoxyethyl, 1-methyl-1-methoxyethyl, 1-isopropoxyethyl, and 2,2,2-trichloroethyl groups), tetrahydropyranyl group, tetrahydrofuranyl group, 1-hydroxyalkyl groups (e.g., 1-hydroxyethyl, 1-hydroxyhexyl, 1-hydroxydecyl, and 1-hydroxyhexadecyl groups), and other groups that can form an acetal group or hemi-acetal group with a hydroxyl group; acyl groups (e.g., formyl, acetyl, propionyl, butyryl, isobutyryl, valeryl, pivaloyl, and other $C_1$–$C_6$ aliphatic acyl groups; acetoacetyl group; benzoyl, naphthoyl, and other aromatic acyl groups), alkoxycarbonyl groups (e.g., methoxycarbonyl, ethoxycarbonyl, t-butoxycarbonyl, and other $C_1$–$C_4$ alkoxy carbonyl groups), aralkyloxycarbonyl groups (e.g., benzyloxycarbonyl group, and p-methoxybenzyloxycarbonyl group), substituted or unsubstituted carbamoyl groups (e.g., carbamoyl, methylcarbamoyl, and phenylcarbamoyl groups), dialkylphosphinothioyl groups (e.g., dimethylphosphinothioyl groups), diarylphosphinothioyl groups (e.g., diphenylphosphinothioyl group), substituted silyl groups (e.g., trimethylsilyl, t-butyldimethylsilyl, tribenzylsilyl, and triphenylsilyl groups), and when the molecule contains two or more hydroxyl groups (including hydroxymethyl groups), divalent hydrocarbon groups which may have a substituent (e.g., methylene, ethylidene, isopropylidene, cyclopentylidene, cyclohexylidene, and benzylidene groups). Preferred protective groups for hydroxyl group include, for example, $C_1$–$C_4$ alkyl groups; substituted methyl groups, substituted ethyl groups, 1-hydroxylalkyl groups, and other groups that can form an acetal group or hemi-acetal group with a hydroxyl group; acyl groups, $C_1$–$C_4$ alkoxy-carbonyl groups, substituted or unsubstituted carbamoyl groups, substituted silyl groups, and divalent hydrocarbon groups which may have a substituent.

Protective groups for amino group in $R^c$, $R^d$ and $R^e$ include the aforementioned alkyl groups, aralkyl groups, acyl groups, alkoxycarbonyl groups, aralkyloxycarbonyl groups, dialkylphosphinothioyl groups, diarylphoshinothioyl groups mentioned as the protective groups for hydroxyl group. Preferred protective groups for amino group are, for example, $C_1$–$C_4$ alkyl groups, $C_1$–$C_6$ aliphatic groups, aromatic acyl groups, and $C_1$–$C_4$ alkoxy-carbonyl groups.

As examples of protective groups for carboxyl group in $R^c$, $R^d$ and $R^e$, there may be mentioned alkoxy groups (e.g., methoxy, ethoxy, butoxy, and other $C_1$–$C_6$ alkoxy groups), cycloalkyloxy groups, aryloxy groups (e.g., phenoxy group), aralkyloxy groups (e.g., benzyloxy group), trialkylsilyloxy groups (e.g., trimethylsilyloxy group), amino groups which may have a substituent (e.g., amino group; methylamino group, dimethylamino group and other mono- or di-$C_1$–$C_6$ alkylamino groups), hydrazino group, alkoxycarbonylhydrazino groups, and aralkyloxycarbonylhydrazino groups. Preferred protective groups for carboxyl group are $C_1$–$C_6$ alkoxy groups (in particular $C_1$–$C_4$ alkoxy groups), and mono- or di-$C_1$–$C_6$ alkylamino groups (especially, mono- or di-$C_1$–$C_4$ alkyalamino groups), for instance.

Acyl groups in $R^c$, $R^d$ and $R_e$ include, but are not limited to, saturated aliphatic $C_2$–$C_5$ acyl groups (e.g., acetyl, propionyl, and butyryl groups), cycloalkylcarbonyl groups (e.g., cyclopentylcarbonyl, and cyclohexylcarbonyl groups), and arylcarbonyl groups (e.g., benzoyl group). Of these groups, acetyl group and propionyl group, in particular acetyl group, is preferred.

The substituents $R^a$ and $R^b$ in the groups represented by the formula (2) are the same with $R^a$ and $R^b$ in the formula (1).

Preferred examples of $R^c$, $R^d$ and $R^e$ include a hydrogen atom, $C_1$–$C_4$ alkyl groups, a hydroxyl group which may be protected by a protective group, a hydroxymethyl group which may be protected by a protective group, and a carboxyl group which may be protected by a protective group.

In the compounds represented by the formula (1) [as well as in the compounds represented by the formulae (1b), (3), (8), (11), (12a) and (12b) as mentioned later], the other carbon atoms (carbon atoms constituting methylene groups in the formula) of carbon atoms constituting the adamantane skeleton than those at the bridgehead positions may have a substituent. Such substituents include, but are not limited to, oxo group, alkyl groups (e.g., methyl group and other $C_1$–$C_4$ alkyl groups), acyl groups (acetyl group and other $C_2$–$C_5$ aliphatic acyl groups, benzoyl group and other arylcarbonyl groups), hydroxyl groups which may be protected by a protective group as described above [e.g., hydroxyl group, alkoxy groups (e.g., methoxy group and other $C_1$–$C_4$ alkoxy groups, substituted methyloxy groups, substituted ethyloxy groups), acyloxy groups (acetoxy and other $C_2$–$C_6$ aliphatic acyloxy groups, acetoacetyloxy group, benzoyloxy group and other arylcarbonyloxy groups)], carboxyl groups which may be protected by a protective group as mentioned above [e.g., carboxyl group, and alkoxycarbonyl groups (e.g., methoxycarbonyl, ethoxycarbonyl, and other $C_1$–$C_4$ alkoxycarbonyl groups)], amino groups which may be protected by a protective group as described above, halogen atoms (e.g., fluorine, chlorine, and bromine atoms) and cyano group.

When $R^a$ is a hydrogen atom or a methyl group and $R^b$ is a methyl group in the inventive compounds, a hydroxyl group which is protected by a protective group, a hydroxymethyl group which may be protected by a protective group, an amino group which may be protected by a protective group, a carboxyl group which may be protected by a protective group, a nitro group, an acyl group or a group represented by the formula (2) is bonded to at least one carbon atom constituting the adamantane skeleton. When one of $R^a$ and $R^b$ is a methyl group and the other is an ethyl group, at least one substituent, in addition to the HO—C($R^a$)($R^b$)— group (hereinafter may be referred to as the "C-substituted hydroxymethyl group") indicated in the formula (1), is bonded to the adamantane ring.

If a plurality of the C-substituted hydroxymethyl groups in the same molecule in the inventive compounds, they may be either the same group or different groups.

Preferred adamantanemethanol derivatives in the invention include, in the formula (1), (a) compounds where $R^b$ is a hydrocarbon group having a methine carbon atom at a bonding site with the adjacent carbon atom [e.g., compounds where $R^a$ is a hydrogen atom, a $C_1$–$C_{10}$ alkyl group (preferably a $C_1$–$C_6$ alkyl group, particularly a $C_1$–$C_4$ alkyl group) or a 3- to 8-membered cycloalkyl group, and $R^b$ is a $C_3$–$C_{10}$ alkyl group (preferably a $C_3$–$C_6$ alkyl group, particularly a $C_3$–$C_4$ alkyl group) or a 3- to 8-membered cycloalkyl group, which has a methine carbon atom at a bonding site with the adjacent carbon atom], (b) compounds where each of $R^a$ and $R^b$ is a $C_2$–$C_{10}$ alkyl group (preferably a $C_2$–$C_6$ alkyl group, particularly at least one is a $C_3$–$C_6$ alkyl group) or a 3- to 8-membered cycloalkyl group, (c) compounds where $R^a$ and $R^b$ are the same hydrocarbon group [among them, compounds where $R^a$ and $R^b$ are both a $C_1$–$C_{10}$ alkyl group (preferably a $C_1$–$C_6$ alkyl group, particularly a $C_1$–$C_4$ alkyl group) or a 3- to 8-membered cycloalkyl group], (d) compounds each having a hydroxyl group protected by a protective group, which hydroxyl group is bonded to at least one carbon atom constituting the adamantane skeleton (e.g., at least one of $R^c$, $R^d$ and $R^e$ is a hydroxyl group protected by a protective group) [among them, compounds where each of $R^a$ and $R^b$ is a $C_1$–$C_{10}$ alkyl group (preferably a $C_1$–$C_6$ alkyl group, particularly a $C_1$–$C_4$ alkyl group) or a 3- to 8-membered cycloalkyl group], (e) compounds represented by the formula (1c) (e.g., compounds where $R^d$ is a hydroxyl group which may be protected by a protective group) [among them, compounds where each of $R^a$ and $R^b$ is a $C_1$–$C_{10}$ alkyl group, (preferably a $C_1$–$C_6$ alkyl group, more preferably a $C_1$–$C_3$ alkyl group, particularly a $C_1$–$C_2$ alkyl group) or a 3- to 8-membered cycloalkyl group], and (f) compounds where at least two of $R^c$, $R^d$ and $R^e$ are, identical to or different from each other, a group selected from hydroxyl groups which may be protected by a protective group and the groups represented by the formula (2) [among them, compounds where each of $R^a$ and $R^b$ is a $C_1$–$C_{10}$ alkyl group (preferably a $C_1$–$C_6$ alkyl group, more preferably a $C_1$–$C_3$ alkyl group, particularly a $C_1$–$C_2$ alkyl group) or a 3- to 8-membered cycloalkyl group].

Typical examples of the compounds represented by the formula (1) include α-isopropyl-1-adamantanemethanol (α-isopropyl-tricyclo[3.3.1.1$^{3,7}$]decane-1-methanol), 3-hydroxy-α-isopropyl-1-adamantanemethanol, α-isopropyl-α-methyl-1-adamantanemethanol, α-ethyl-α-isopropyl-1-adamantanemethanol, α-ethyl-3-hydroxy-α-isopropyl-1-adamantanemethanol, 3-chloro-α-ethyl-αmethyl-1-adamantanemethanol, α-ethyl-α,3-dimethyl-1-adamantanemethanol, α-ethyl-α,3,5-trimethyl-1-adamantanemethanol, α-ethyl-3-hydroxy-α-methyl-1-adamantanemethanol, α-ethyl-3,5-dihydroxy-α-methyl-1-adamantanemethanol, α-ethyl-3,5,7-trihydroxy-α-methyl-1-adamantanemethanol, α-ethyl-3-hydroxymethyl-α-methyl-1-adamantanemethanol, 3-amino-α-ethyl-α-methyl-1-adamantanemethanol, 3-carboxy-αethyl-α-methyl-1-adamantanemethanol, 3,5-dicarboxy-α-ethyl-α-methyl-1-adamantanemethanol, 3,5,7-tricarboxy-α-ethyl-α-methyl-1-adamantanemethanol, α-ethyl-α-methyl-3-nitro-1-adamantanemethanol, 3-acetyl-α-ethyl-α-methyl-1-adamantanemethanol, α,α'-diethyl-α,α'-dimethyl-1,3-adamantanedimethanol, 3-chloro-α-isopropyl-α-methyl-1-adamantanemethanol, α-isopropyl-α,3-dimethyl-1-adamantanemethanol, α-isopropyl-α,3,5-trimethyl-1-adamantanemethanol, 3-hydroxy-α-isopropyl-α-methyl-1-adamantanemethanol, 3,5-dihydroxy-α-isopropyl-α-methyl-1-adamantanemethanol, 3,5,7-trihydroxy-α-isopropyl-α-methyl-1-adamantanemethanol, 3-hydroxymethyl-α-isopropyl-α-methyl-1-adamantanemethanol, 3-amino-α-isopropyl-α-methyl-1-adamantanemethanol, 3-carboxy-α-isopropyl-α-methyl-1-adamantanemethanol, 3,5-dicarboxy-α-isopropyl-α-methyl-1-adamantanemethanol, 3,5,7-tricarboxy-α-isopropyl-α-methyl-1-adamantanemethanol, α-isopropyl-α-methyl-3-nitro-1-adamantanemethanol, 3-acetyl-α-isopropyl-α-methyl-1-adamantanemethanol, α,α'-diisopropyl-α,α'-dimethyl-1,3-adamantanedimethanol, α,α-diethyl-1-adamantanemethanol, 3-chloro-α,α-diethyl-1-adamantanemethanol, α,α-diethyl-3-methyl-1-adamantanemethanol, α,α-diethyl-3,5-dimethyl-1-adamantanemethanol, α,α-diethyl-3-hydroxy-1-adamantanemethanol, α,α-diethyl-3,5-dihydroxy-1-adamantanemethanol, α,α-diethyl-3,5,7-trihydroxy-1-adamantanemethanol, α,α-diethyl-3-hydroxymethyl-1-adamantanemethanol, 3-amino-α,α-diethyl-1-adamantanemethanol, 3-carboxy-α,α-diethyl-1-adamantanemethanol, α,α-diethyl-3,5-dicarboxy-1-adamantanemethanol, α,α-diethyl-3,5,7-tricarboxy-1-adamantanemethanol, α,α-diethyl-3-nitro-1-adamantanemethanol, 3-acetyl-α,α-diethyl-1-adamantanemethanol, α,α,α',α'-tetraethyl-1,3-adamantanemethanol, αα-dipropyl-1-adamantanemethanol, αα-diisopropyl-1-adamantanemethanol, α,α-dibutyl-1-adamantanemethanol, α-s-butyl-α-methyl-1-adamantanemethanol, α-s-butyl-3-hydroxy-α-methyl-1-adamantanemethanol, α-s-butyl-3-hydroxymethyl-α-methyl-1-adamantanemethanol, α-s-butyl-3-carboxy-α-methyl-1-adamantanemethanol, α-methyl-α-(1-methylbutyl)-1-adamantanemethanol, 3-hydroxy-α-methyl-α-(1-methylbutyl)-1-adamantanemethanol, 3-hydroxymethyl-α-methyl-α-(1-methylbutyl)-1-adamantanemethanol, 3-carboxy-α-methyl-α-(1-methylbutyl)-1-adamantanemethanol, α-(1-ethylpropyl)-α-methyl-1-adamantanemethanol, α-(1-ethylpropyl)-3-hydroxy-α-methyl-1-adamantanemethanol, α-(1-ethylpropyl)-3-hydroxymethyl-α-methyl-1-adamantanemethanol, α-(1-ethylpropyl)-3-carboxy-α-methyl-1-adamantanemethanol, α-methyl-α-(1-methylpentyl)-1-adamantanemethanol, 3-hydroxy-α-methyl-α-(1-methylpentyl)-1-adamantanemethanol, 3-hydroxymethyl-α-methyl-α-(1-methylpentyl)-1-adamantanemethanol, 3-carboxy-α-methyl-α-(1-methylpentyl)-1-adamantanemethanol, α-(1-ethylbutyl)-α-methyl-1-adamantanemethanol, α-(1-ethylbutyl)-3-hydroxy-α-methyl-1-adamantanemethanol, α-(1-ethylbutyl)-3-hydroxymethyl-α-methyl-1-adamantanemethanol, α-(1-ethylbutyl)-3-carboxy-α-methyl-1-adamantanemethanol, α-cyclopropyl-α-methyl-1-adamantanemethanol, α-cyclopropyl-3-hydroxy-α-methyl-1-adamantanemethanol, α-cyclopropyl-3-hydroxymethyl-α-methyl-1-adamantanemethanol, 3-carboxy-α-cyclopropyl-α-methyl-1-adamantanemethanol, α-cyclopentyl-α-methyl-1-adamantanemethanol, α-cyclopentyl-3-hydroxy-α-methyl-1-adamantanemethanol, α-cyclopentyl-3-hydroxymethyl-α-methyl-1-adamantanemethanol, 3-carboxy-α-cyclopentyl-α-methyl-1-adamantanemethanol, α-cyclohexyl-α-methyl-1-adamantanemethanol, α-cyclohexyl-3-hydroxy-α-methyl-1-adamantanemethanol α-cyclohexyl-3-hydroxymethyl-α-methyl-1-adamantanemethanol, 3-carboxy-α-cyclohexyl-α-methyl-1-adamantanemethanol, α-methyl-α-propyl-1-adamantanemethanol, 3-hydroxy-α- methyl-α-propyl-1-adamantanemethanol, 3-hydroxymethyl-α-methyl-α-propyl-1-adamantanemethanol, 3-carboxy-α-methyl-α-propyl-1-adamantanemethanol, α-butyl-α-methyl-1-adamantanemethanol, α-butyl-3-hydroxy-α-methyl-1-adamantanemethanol, α-butyl-3-hydroxymethyl-α-methyl-1adamantanemethanol, α-butyl-3-carboxy-α-methyl-1-adamantanemethanol, α-isobutyl-α-methyl-1-adamantanemethanol, 3-hydroxy-α-isobutyl-α-methyl-1-adamantanemethanol, 3-hydroxymethyl-α-isobutyl-α-methyl-1-adamantanemethanol, 3-carboxy-α-isobutyl-α-methyl-1-adamantanemethanol, α-methyl-α-pentyl-1-adamantanemethanol, 3-hydroxy-α-methyl-α-pentyl-1-adamantanemethanol, 3-hydroxymethyl-α-methyl-α-pentyl-1-adamantanemethanol, 3-carboxy-α-methyl-α-pentyl-1-adamantanemethanol, α-hexyl-α-methyl-1-adamantanemethanol, α-hexyl-3-hydroxy-α-methyl-1-adamantanemethanol, α-hexyl-3-hydroxymethyl-α-methyl-1-adamantanemethanol, 3-carboxy-α-hexyl-α-methyl-1-adamantanemethanol, α-t-butyl-3-hydroxy-α-methyl-1-adamantanemethanol, α,α-dimethyl-3-(2-methoxyethoxymethoxy)-1-adamantanemethanol, α,α-dimethyl-3-methoxyethoxy-1-adamantanemethanol, α,α-dimethyl-3-methylthiomethoxy-1-adamantanemethanol, α,α-dimethyl-3-[2-(trimethylsilyl)ethoxymethoxyl]-1-adamantanemethanol, α,α-dimethyl-3-methoxy-1-adamantanemethanol, 3-acetyloxy-α,α-dimethyl-1-adamantanemethanol, 3-acetoacetyloxy-α,α-dimethyl-1-adamantanemethanol, α,α-diethyl-3-(2-methoxyethoxymethoxy)-1-adamantanemethanol, α,α-diethyl-3-methoxymethoxy-1-adamantanemethanol, α,α-diethyl-3-methylthiomethoxy-1-adamantanemethanol, α,α-diethyl-3-[2-(trimethylsilyl)ethoxymethoxy]-1-adamantanemethanol, α,α-diethyl-3-methoxy-1-adamantanemethanol, 3-acetyloxy-α,α-diethyl-1-adamantanemethanol, 3-acetoacetyloxy-α,α-diethyl-1-adamantanemethanol, 5-hydroxy-α,α,α',α'-tetramethyl-1,3-adamantanedimethanol, 5-(2-methoxyethoxymethoxy)-α,α,α',α'-tetramethyl-1,3-adamantanedimethanol, 5-methoxymethoxy-α,α,α',α'-tetramethyl-1,3-adamantanedimethanol, 5-methylthiomethoxy-α,α,α',α'-tetramethyl-1,3-adamantanedimethanol, 5-[2-(trimethylsilyl)ethoxymethoxy]-α,α,α',α'-tetramethyl-1,3-adamantanedimethanol, 5-methoxy-α,α,α',α'-tetramethyl-1,3-adamantanedimethanol, 5-acetyloxy-α,α,α',α'-tetramethyl-1,3-adamantanedimethanol, 5-acetoacetyloxy-α,α,α',α'-tetramethyl-1,3-adamantanedimethanol, 5-hydroxy-α,α,α',α'-tetraethyl-1,3-adamantanedimethanol, 5-(2-methoxyethoxymethoxy)-α,α,α',α'-tetraethyl-1,3-adamantanedimethanol, 5-methoxymethoxy-α,α,α',α'-tetraethyl-1,3-adamantanedimethanol, 5-methylthiomethoxy-α,α,α',α'-tetraethyl-1,3-adamantanedimethanol, 5-[2-(trimethylsilyl)ethoxymethoxy]-α,α,α',α'-tetraethyl-1,3-adamantanedimethanol, 5-methoxy-α,α,α',α'-tetraethyl-1,3-adamantanedimethanol, 5-acetyloxy-α,α,α',α'-tetraethyl-1,3-adamantanedimethanol, 5-acetoacetyloxy-α,α,α',α'-tetraethyl-1,3-adamantanedimethanol, 3,5,7-trihydroxy-α,α-dimethyl-1-adamantanemethanol, 5,7-dihydroxy-α,α,α',α'-tetramethyl-1,3-adamantanedimethanol, 7-hydroxy-α,α,α',α',α",α"-hexamethyl-1,3,5-adamantanetrimethanol, and α,α,α',α',α",α",α"',α"'-octamethyl-1,3,5,7-adamantanetetramethanol.

Of the inventive adamantanemethanol derivatives, when those having a specific substituent on a carbon atom adjacent to a hydroxyl group (α-position carbon atom), namely, those having a hydrocarbon group containing a methine carbon atom at a bonding site with the α-position carbon atom or a hydrocarbon group having a comparatively long chain are converted into, for example, esters of carboxylic acids (e.g., acrylic acid), they are insoluble in an alkali, but are very highly degradable by acids to give carboxylic acids being alkali-soluble. Therefore, the above compounds are expected to be used as monomers of their materials for resist resins.

In this connection, these compounds are quite different from α,α-dimethyl-1-adamantanemethanol, a known compound, in degradability by acids when both are introduced to esters of carboxylic acids. The reason for this can be estimated from heat of formation of vinyladamantane derivatives corresponding to dehydrated produces of adamantanemethanol derivatives having, at the α-position, a hydrocarbon group containing a hydrogen atom bonded to a carbon atom adjacent to the α-position carbon atom. To be more specific, it is projected that the smaller the heat of formation of the vinyladamantane derivatives is, the easier the esters of the corresponding adamantanemethanol derivatives are decomposed. By way of illustration, 1-vinyladamantane, a vinyladamantane derivative corresponding to α-methyl-1-adamantanemethanol, has a heat of formation of 6.3 kcal/mol, and 1-isopropenyladamantane corresponding to α,α-dimethyl-1-adamantanemethanol, has a heat of formation of −3.0 kcal/mol. On the contrary, 1,2-dimethyl-1-propenyladamantane corresponding to α-isopropyl-α-methyl-1-adamantanemethanol, and 1,2-dimethyl-1-butenyladamantane corresponding to α-s-butyl-α-methyl-1-adamantanemethanol each have heat of formation of −9.0 kcal/mol and −7.0 kcal/mol, respectively, which is extremely smaller than that of the former two compounds. Accordingly, it is estimated that an ester of α-isopropyl-α-methyl-1-adamantanemethanol and an ester of α-s-butyl-α-methyl-1-adamantanemethanol are very easily decomposed (decarboxylated). The aforementioned heat of formation is obtained by the use of a computational program for heat of formation, "MOPAC PM-3".

Of the inventive compounds, adamantanemethanol derivatives having a hydroxyl group protected by a protective group, which is bonded to at least one carbon atom constituting the adamantane skeleton (e.g., a 3-position, 5-position or 7-position bridgehead carbon atom), as the preferred adamantanemethanol derivatives (d), have various advantages as follows: When they are introduced to esters of carboxylic acids (e.g., acrylic acid) as described above and then derived to polymers, (i) the hydrophilic property, adhesion to substrates and other properties can be improved and adjusted by the proper selection of the protective group, (ii) side reactions in polymerization can be inhibited and their molecular weights can be controlled with facility and the handling property can be improved, as compared with, for example, compounds having a free hydroxyl group bonded thereto, and (iii) the hydroxyl group can be converted to a free hydroxyl group by deprotection, where necessary. For instance, compounds each having a hydroxyl group protected by a group that can form an acetal group or hemi-acetal group with the hydroxyl group or by a substituted silyl group can readily by deprotected with weak energy to form a free hydroxyl group, and thus they can be used as materials for highly sensitive photosensitive resins. Therefore, the above compounds are useful as monomers or their materials for resist resins and other highly functional polymers.

Furthermore, of the inventive compounds, in compounds having two C-substituted hydroxymethyl groups at the bridgehead positions of the adamantane skeleton, and a substituent at least one bridgehead position of the other bridgehead positions, as in the preferred adamantanemethanol derivatives (e) (i.e., the compounds represented by the formula (1c)), the selection of the substituent can impart various functions to the compounds or can adjust functions of the compounds. For instance, of the preferred adamantanemethanol derivatives (e), compounds are taken as sample, which compounds each have, at least at one bridgehead position of the other bridgehead positions than bonding sites of the C-substituted hydroxymethyl groups, a hydroxyl group which may be protected by a protective group, a hydroxymethyl group which may be protected by a protective group, an amino group which may be protected by a protective group, a carboxyl group which may be protected by a protective group, a nitro group, an acyl group, or a compound represented by the formula (2), or another oxygen-containing or nitrogen-containing functional group (in particular, a hydroxyl group which may be protected by a protective group). When these compounds are polymerized after converting the C-substituted hydroxymethyl groups into, for example, C-substituted acryloyloxymethyl groups, the resultant polymers can have high hydrophilicity, and markedly improved adhesion or adhesive property to substrates or the like, as compared with polymers obtained from, for example, α,α,α',α'-tetramethyl-1,3-adamantanedimethanol, a known compound, by converting into C-substituted acryloyloxymethyl group and polymerizing. Therefore, the former inventive compounds are very useful as, for example, materials for photoresist resins.

Of the other compounds than above, adamantanemethanol derivatives each having a hydroxyl group, a hydroxymethyl group, a carboxyl group or another additional functional group on the adamantane ring can be enhanced in functions or can have a variety of additional functions or controlled functions. In addition and advantageously, the inventive compounds are expected to be used as, for instance, intermediates of pharmaceuticals.

Production Processes for Adamantanemethanol Derivatives

In the production process 1 according to the invention, the substituents $R^a$ and $R^b$ in $R^x$ and $R^y$ in the formulae (3) and (4) have the same meanings as defined in $R^a$ and $R^b$ in the formula (1). The halogen atoms, alkyl groups, protective groups for hydroxyl group, protective groups for hydroxymethyl group, protective groups for amino group, protective groups for carboxyl group, and acyl groups include corresponding substituents and the like exemplified in the aforementioned $R^c$, $R^d$ and $R^e$.

The metal atom in M in the formula (4) includes, but is not limited to, lithium and other alkali metal atoms, cerium, titanium, copper and other transition metal atoms. The metal atom may have a ligand. The term "ligand" as used in the present description also includes an atom or atomic group corresponding to a cation in an ate-complex. As examples of the ligand, there may be mentioned chlorine atom and other halogen atoms, isopropoxy group and other alkoxy groups, diethylamino group and other dialkylamino groups, cyano group, alkyl groups, and lithium atom and other alkali metal atoms (as cations in ate-complexes). In the formula (5), halogen atoms represented by Y include chlorine, bromine and iodine atoms. Typical examples of the organometallic compounds represented by the formula (4) include dimethyldiisopropoxytitanium and other organo-titanium compounds (e.g., ate-complexes of organo-titanium), organo-magnesium compounds (e.g., Grignard reagents), and organo-lithium compounds.

The proportion of the compound represented by the formula (4) is, for example, about 0.7 to 3 moles, and preferably about 0.9 to 1.5 moles relative to 1 mole of the adamantane derivative represented by the formula (3).

The inventive process is usually carried out in an organic solvent. The organic solvent has only to be an inert solvent to the reaction, and includes, but is not limited to, diethyl ether, 1,2-dimethoxyethane, tetrahydrofuran and other ethers; heptane, hexane, octane and other aliphatic hydrocarbons.

The reaction temperature can be chosen from adequate ranges, for example, from about −100° C. to about 150° C., according to the species of the reactants or the like. By way of illustration, when M is a metal atom (e.g., lithium) in the compound represented by the formula (4), the reaction temperature is from about −100° C. to about 20° C. When a compound where M is a group represented by the formula (5) is used as the compound represented by the formula (4), the reaction temperature is, for example, from about 0° C. to about 150° C., and preferably from about 20° C. to about 100° C.

The reaction can be performed in a batch system, semi-batch system, continuous system or another conventional system. After the completion of the reaction, a target reaction product can usually be obtained by adding an aqueous solution containing an acid (e.g., hydrochloric acid) or a salt (e.g., ammonium chloride) to the reaction mixture for quenching, and adjusting the alkalinity or acidity of the mixture where necessary, and subjecting the mixture to a conventional separation and purification means. Such separation and purification means include filtration, concentration, extraction, distillation, crystallization, recrystallization, and column chromatography.

The compounds represented by the formula (4) can be prepared in a conventional manner. For instance, compounds where M in the formula (4) is a group represented by the formula (5) can be prepared by a conventional process for the preparation of a so-called Grignard reagent. To be more specific, the compounds can be prepared by adding a small portion of iodine, ethyl bromide or another accelerant to a mixture containing a magnesium metal, part of a compound represented by the following formula (7):

$$R^y-Y \qquad (7)$$

(wherein $R^y$ and Y have the same meanings as defined above) and an organic solvent to start the reaction, and then adding the rest of the compound represented by the formula (7) to carry on the reaction. As the organic solvent, solvents to be used in the above inventive process can be employed. The proportion of the magnesium metal is, for example, about 1 to 1.5 moles relative to 1 mole of the compound represented by the formula (7), and the reaction temperature is, for instance, from about 0° C. to about 100° C. The compounds represented by the formula (4) thus obtained can be used in the inventive process without isolation.

According to the inventive process, the novel adamantanemethanol derivatives can be produced by simple operations in good yields. In this connection, when the adamantane derivatives represented by the formula (3) each have a plurality of acyl groups [$R^xCO$ group] in the molecule, adamantanemethanol derivatives each having a plurality of the group represented by the formula (2) can be obtained by the selection of reaction conditions (e.g., by increasing the amount of the compound represented the formula (4)).

Preparation of Adamantane Derivatives of the Formula (3)

Adamantane derivatives represented by the formula (3) to be used as a material in the inventive production process 1 can be prepared, for instance, by: reacting a compound represented by the following formula (8):

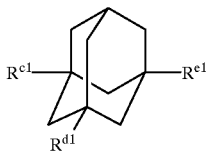

(8)

(wherein $R^{c1}$, $R^{d1}$ and $R^{e1}$ have the same meanings as defined above) with an acylating agent comprising (A) a 1,2-dicarbonyl compound represented by the following formula (9):

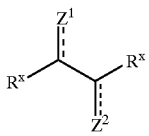

(9)

(wherein $Z^1$ and $Z^2$ are each, identical to or different from each other, an oxygen atom or a hydroxyl group, and $R^x$ has the same meaning as defined above) or its hydroxy reductant, (B) oxygen, and (C) at least one compound selected from (C1) a metallic compound and (C2) an imide compound represented by the following formula (10):

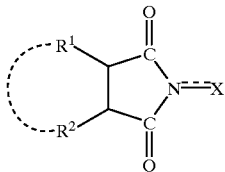

(10)

(wherein each of $R^1$ and $R^2$ is, identical to or different from each other, and hydrogen atom, a halogen atom, an alkyl group, an aryl group, a cycloalkyl group, a hydroxyl group, an alkoxy group, a carboxyl group, an alkoxycarbonyl group, or an acyl group, where $R^1$ and $R^2$ may be combined to form a double bond, or an aromatic or non-aromatic ring; X is an oxygen atom or a hydroxyl group; and one or two N-substituted cyclic imido groups indicated in the formula (10) may be bonded to the aforementioned $R^1$, $R^2$, or to the double bond or aromatic or non-aromatic ring formed together by $R^1$ and $R^2$).

The $Z^1$ and $Z^2$ are each an oxygen atom or a hydroxyl group, and the bond between the carbon atom and $Z^1$ or $Z^2$ is a single bond or a double bond.

Typical examples of the 1,2-dicarbonyl compound include biacetyl (2,3-butanedione), 2,3-pentanedione, 3,4-hexanedione, bibenzoyl (benzyl), acetylbenzoyl, and other α-diketones. Representative examples of the hydroxy reductant of the 1,2-dicarbonyl compound include acetoin, benzoin, and other α-keto-alcohols; 2,3-butanediol, 2,3-pentanediol, and other vicinal diols.

The oxygen (B) may be either molecular oxygen or active oxygen (oxygen radical). The molecular oxygen includes, but is not limited to, pure oxygen, and oxygen diluted with an inert gas such as nitrogen, helium, argon or carbon dioxide, as well as air. As the oxygen (B), molecular oxygen is frequently used.

Metallic elements to constitute the metallic compound (C1) are not especially limited, and can be any metallic element of Groups 1 to 15 of the Periodic Table of Elements. In the present description, the term "metallic element" also means and includes boron, B. Examples of the metallic elements include, of the Periodic Table of Elements, Group 1 elements (e.g., Li, Na, K), Group 2 elements (e.g., Mg, Ca, Sr, Ba), Groups 3 elements (e.g., Sc, lanthanoid elements, actinoid elements), Group 4 elements (e.g., Ti, Zr, Hf), Group 5 elements (e.g., V), Group 6 elements (e.g., Cr, Mo, W), Group 7 elements (e.g., Mn), Group 8 elements (e.g., Fe, Ru), Group 9 elements (e.g., Co, Rh), Group 10 elements (e.g., Ni, Pd, Pt), Group 11 elements (e.g., Cu), Group 12 elements (e.g., Zn), Groups 13 elements (e.g., B, Al, In), Group 14 elements (e.g., Sn, Pb), Group 15 elements (e.g., Sb, Bi) and the like. Preferred metallic elements include transition metal elements (elements of Groups 3 to 12 of the Periodic Table of Elements). Among them, elements of the Groups 5 to 11 of the Periodic Table of Elements are preferred, of which Group 5 elements and Group 9 elements are typically preferred. Especially, Co, V or the like can advantageously be used. The valence of the metallic element is not particularly limited, and may range about from 0 to 6.

As the metallic compound (C1), there may be mentioned, for example, elementary substances, hydroxides, oxides (including complex oxides), halides (fluorides, chlorides, bromides, and iodides), salts of oxoacids (e.g., nirates, sulfates, phosphates, borates, and carbonates), oxoacids, isopolyacids, heteropolyacids, and other inorganic compounds of the aforementioned metallic elements; salts of organic acids (e.g., acetates, propionates, prussiates, naphthenates, and stearates), complexes, and other organic compounds of the metallic elements. Ligands constituting the complexes include OH (hydroxo), alkoxy (e.g., methoxy, ethoxy, propoxy, and butoxy), acyl (e.g., acetyl, and propionyl), alkoxycarbonyl (e.g., methoxycarbonyl, and ethoxycarbonyl), acetylacetonato, cyclopentadienyl group, halogen atoms (e.g., chlorine, and bromine), CO, CN, oxygen atom, $H_2O$ (aquo), phosphine (triphenylphosphine and other triarylphosphines and other) phosphorus compounds, $NH_3$ (ammine), NO, $NO_2$ (nitro), $NO_3$ (nitrato), ethylenediamine, diethylenetriamine, pyridine, phenanthroline, and other nitrogen-containing compounds.

Concrete examples of the metallic compound (C1) include, by taking cobalt compounds as example, cobalt hydroxide, cobalt oxide, cobalt chloride, cobalt bromide, cobalt nitrate, cobalt sulfate, cobalt phosphate, and other inorganic compounds; cobalt acetate, cobalt naphthenate, cobalt stearate, and other salts of organic acids; cobalt acetylacetonato, and other complexes, and other divalent or trivalent cobalt compounds. As illustrative vanadium compounds, there may be mentioned vanadium hydroxide, vanadium oxide, vanadium chloride, vanadyl chloride, vanadium sulfate, vanadyl sulfate, sodium vanadate, and other inorganic compounds; vanadium acetylacetonato, vanadyl acetylacetonato, and other complexes, and other vanadium compounds having a valence of 2 to 5. Examples of compounds of the other metallic elements include compounds corresponding to the above-mentioned cobalt or vanadium compounds. Each of the metallic compounds (C1) can be used singly or in combination.

The ratio of the metallic compound (C1) to the 1,2-dicarbonyl compound or its hydroxy reductant (A) is, for example, such that the former (C1)/the latter (A) (by mole) equals about 0 to 0.1, preferably about 0.001 to 0.05, and more preferably about 0.002 to 0.02.

Of the substituents $R^1$ and $R^2$ in the imide compound (C2) represented by the formula (10), the halogen atom includes iodine, bromine, chlorine and fluorine. The alkyl group include, for instance, methyl, ethyl, propyl, isopropyl, butyl, isobutyl, s-butyl, t-butyl, hexyl, and decyl groups, and other straight- or branched-chain alkyl groups each having about 1 to 10 carbon atoms. As preferred alkyl groups, there may be mentioned, for instance, alkyl groups each having about 1 to 6 carbon atoms, and more preferably lower alkyl groups each having about 1 to 4 carbon atoms.

The aryl group includes phenyl, and naphthyl groups, for example; and the illustrative cycloalkyl group includes cyclopentyl, and cyclohexyl groups. As the alkoxy group, there may be mentioned, for example, methoxy, ethoxy, isopropoxy, butoxy, t-butoxy, hexyloxy, and other alkoxy groups each having about 1 to 10 carbon atoms, preferably about 1 to 6 carbon atoms, of which lower alkoxy groups each having about 1 to 4 carbon atoms are especially preferred.

Examples of the alkoxycarbonyl group include methoxycarbonyl, ethoxycarbonyl, isopropoxycarbonyl, butoxycarbonyl, t-butoxycarbonyl, hexyloxycarbonyl, and other alkoxycarbonyl groups each having about 1 to 10 carbon atoms in the alkoxy moiety. Preferred alkoxycarbonyl groups include alkoxycarbonyl groups each having about 1 to 6 carbon atoms in the alkoxy moiety, and especially lower alkoxycarbonyl groups each having about 1 to 4 carbon atoms in the alkoxy moiety. As the illustrative acyl group, there may be mentioned formyl, acetyl, propionyl, butyryl, isobutyryl, valeryl, isovaleryl, pivaloyl, and other acyl groups each having about 1 to 6 carbon atoms.

The substituents $R^1$ and $R^2$ may be identical to or different from each other. The substituents $R^1$ and $R^2$ in the formula (10) may be combined to form a double bond, or an aromatic or non-aromatic ring. The preferred aromatic or non-aromatic ring is a 5- to 12-membered ring, and especially a 6- to 10-membered ring. It may be either a heterocyclic ring or condensed heterocyclic ring, but it is often a hydrocarbon ring. Such rings include, for example, non-aromatic alicyclic rings (e.g., cyclohexane ring and other cycloalkane rings which may have a substituent, cyclohexene ring and other cycloalkene rings which may have a substituent), non-aromatic bridged rings (e.g., 5-norbornene ring and other bridged hydrocarbon rings which may have a substituent), benzene ring, naphthalene ring and other aromatic rings (including condensed rings) which may have a substituent. The ring is composed of an aromatic ring in many instances. The ring may have a substituent such as an alkyl group, a haloalkyl group, a hydroxyl group, an alkoxy group, a carboxyl group, an alkoxycarbonyl group, an acyl group, a nitro group, a cyano group, an amino group, or a halogen atom.

In the formula (10), X represents an oxygen atom or a hydroxyl group, and the bond between the nitrogen atom, N, and X is a single bond or a double bond.

To $R^1$, $R^2$, or to the double bond or aromatic or non-aromatic ring formed together by $R^1$ and $R^2$, one or two N-substituted cyclic imido groups indicated in the formula (10) may further be bonded. By way of illustration, when $R^1$ or $R^2$ is an alkyl group having 2 or more carbon atoms, the N-substituted cyclic imido group may be formed together with adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or non-aromatic ring, the N-substituted cyclic imido group may be formed with adjacent two carbon atoms constituting the aforementioned ring.

Preferred imide compounds (C2) include compounds represented by the following formulae:

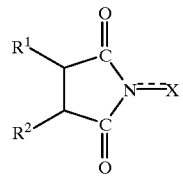 (10a)

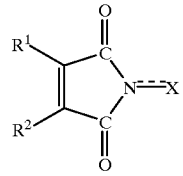 (10b)

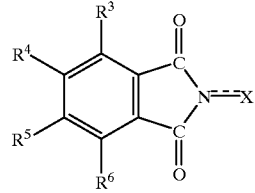 (10c)

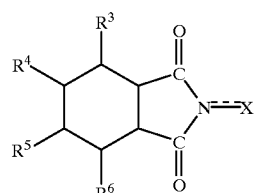 (10d)

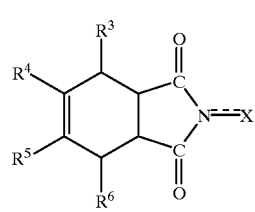 (10e)

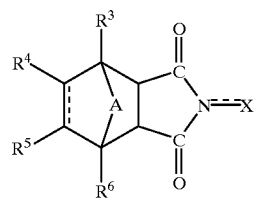 (10f)

(wherein each of $R^3$ to $R^6$ is, identical to or different from each other, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom; where adjacent groups of $R^3$ to $R^6$ may be combined to form an aromatic or non-aromatic ring; in the formula (10f), A represents a methylene group or an oxygen atom, and $R^1$ and $R^2$ have the same meanings as defined above; and one or two N-substituted cyclic imido groups indicated in the formula (10c) may further be bonded to the benzene ring in the formula (10c)).

In the substituents $R^3$ to $R^6$, the alkyl group includes similar alkyl groups to those exemplified above, especially alkyl groups having about 1 to 6 carbon atoms. The haloalkyl group includes trifluoromethyl group and other haloalkyl groups each having about 1 to 4 carbon atoms, and the alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. As the acyl group, there may be mentioned similar acyl groups to those described above, especially acyl groups each having about 1 to 6 carbon atoms, and the illustrative halogen atoms include fluorine, chlorine and bromine atoms. The substituents $R^3$ and $R^6$ are each a hydrogen atom, a lower alkyl group having about 1 to 4 carbon atoms, a carboxyl group, a nitro group, or a halogen atom in many instances. The ring formed together by $R^3$ to $R^6$ includes similar rings to the aforementioned rings which are formed together by $R^1$ and $R^2$. Among them, aromatic or non-aromatic 5- to 12-membered rings are particularly preferred.

As illustrative preferred imide compounds, there may be mentioned N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds (C2) can be prepared by a conventional imidation reaction, for example by a process in which a corresponding acid anhydride is reacted with hydroxylamine, $NH_2OH$, and the acid anhydride group is ring-opened and then is ring-closed to give an imide.

Such acid anhydrides include succinic anhydride, maleic anhydride and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated non-aromatic cyclic polycarboxylic anhydrides (alicyclic polycarboxylic anhydrides), HET anhydride (chlorendic anhydride), himic anhydride, and other bridged cyclic polycarboxylic anhydride (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8:4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred. Each of the imide compounds (C2) represented by the formula (10) can be used singly or in combination.

The proportion of the imide compound (C2) to the 1,2-dicarbonyl compound or its hydroxy reductant (A) is such that the former (C2)/ the latter (A) (by mole) ranges from about 0 to about 1, preferably from about 0.001 to about 0.5, and more preferably from about 0.002 to about 0.2.

The acylating agent has only to contain at least one compound selected from the metallic compound (C1) and the imide compound (C2). To be more specific, the embodiments of the acylating agent of the invention include; (i) an acylating agent composed of the 1,2-dicarbonyl compound or its hydroxy reductant (A), oxygen (B) and the metallic compound (C1), (ii) an acylating agent composed of the 1,2-dicarbonyl compound or its hydroxy reductant (A), oxygen (B) and the imide compound (C2), and (iii) an acylating agent composed of the 1,2-dicarbonyl compound or its hydroxy reductant (A), oxygen (B), the metallic compound (C1), and the imide compound (C2).

In many instances, the use of an acylating agent containing the metallic compound (C1) gives a high conversion rate, and the use of an acylating agent containing the imide compound (C2) yields an acyl group-containing compound with high selectivity. An acylating agent containing the imide compound (C2) has a feature that when used in combination with a hydroxy reductant of the 1,2-dicarbonyl compound as the compound (A), the hydroxy reductant is immediately converted into the corresponding 1,2-dicarbonyl compound in a system, and an acylation reaction proceeds smoothly.

The acylating agent may further comprise additional components including radial generators and radical reaction accelerators in addition to the components (A), (B) and (C). Such additional components include, for instance, halogens (e.g., chlorine, and bromine), peracids (e.g., peracetic acid, and m-chloroperbenzoic acid), and peroxides (e.g., hydrogen peroxide, and hydroperoxide).

In the production of the adamantane derivatives of the formula (3), the amount of the 1,2-dicarbonyl compound or its hydroxy reductant (A) is, for instance, equal to or more than about 1 mole (about 1 to 50 moles), preferably about 1.5 to 20 moles, and more preferably about 3 to 10 moles, to 1 mole of the compound of the formula (8). The 1,2-dicarbonyl compound or its hydroxy reductant (A) can be used as a reaction solvent, as well.

The proportion of the oxygen (B) is, usually, equal to or more than about 0.5 mole (e.g., equal to or more than about 1 mole), preferably from about 1 to about 100 moles, and more preferably from about 2 to about 50 moles per mole of the compound of the formula (8). An excess amount of molecular oxygen to the compound of the formula (8) is used in many cases.

The amount of the metallic compound (C1) is, for example, about 0.00001 to 1 mole, preferably about 0.0001 to 0.1 mole, and more preferably about 0.001 to 0.05 mole, per mole of the compound of the formula (8). The proportion of the imide compound (C2) ranges, for instance, from about 0.00001 to 1 mole, preferably from about 0.001 to 0.7 mole, and more preferably from about 0.01 to 0.5 mole, per mole of the organic substrate.

The reaction is generally performed in an organic solvent. The organic solvent includes, for example, acetic acid, propionic acid, and other organic acids; acetonitrile, propionitrile, benzonitrile, and other nitriles; formamide, acetamide, dimethylformamide (DMF), dimethylacetamide, and other amides; t-butanol, t-amyl alcohol, and other alcohols; hexane, octane, and other aliphatic hydrocarbons; benzene, toluene, and other aromatic hydrocarbons; chloroform, dichloromethane, dichloroethane, carbon tetrachloride, chlorobenzene, trifluoromethylbenzene, and other halogenated hydrocarbons; nitrobenzene, nitromethane, nitroethane, and other nitro compounds; ethyl acetate, butyl acetate, and other esters; diethyl ether, diisopropyl ether, and other ethers; and mixtures of these solvents. As the solvent, acetic acid or another organic acid, benzonitrile or another nitrile, trifluoromethylbenzene or another halogenated hydrocarbon is frequently employed.

The reaction temperature can adequately be selected according to, for instance, the species of the reactants, and is about 0° C. to 300° C., preferably about 30° C. to 250° C., and more preferably about 40° C. to 200° C., for instance. The reaction is frequently performed at about 40° C. to 150° C. The reaction can be carried out at ambient pressure or under pressure. When it is conducted under pressure, the pressure is usually about 1 to 100 atm (e.g. 1.5 to 80 atm), preferably about 2 to 70 atm. The reaction time can adequately be selected within the range, for example, from about 30 minutes to about 48 hours according to the reaction temperature and pressure.

The reaction can be performed in a batch system, semi-batch system, continuous system or another conventional system, in the presence of, or under flow of, oxygen. After the completion of the reaction, reaction products can be separated and purified with facility in a conventional manner including, for example, filtration, concentration, distillation, extraction, crystallization, recrystallization, column chromatography and other separation means, or any combination of these separation means.

According to the acylation process using the acylating agent, an acyl group ($R^xCO$ group) corresponding to the 1,2-dicarbonyl compound is introduced to a bridgehead position of the adamantane derivative represented by the formula (8).

Typical examples of the compounds of the formula (3) thus obtained include 1-acetyladamantane, 1-acetyl-3-chloroadamantane, 1-acetyl-3-methyladamantane, 1-acetyl-3,5-dimethyladamantane, 1-acetyl-3-adamantanol, 1-acetyl-3,5-adamantanediol, 1-aceetyl-3,5,7-adamantanetriol, 1-acetyl-3-hydroxymethyladamantane, 1-acetyl-3-aminoadamantane, 1-acetyl-3-carboxyadamantane, 1-acetyl-3,5-dicarboxyadamantane, 1-acetyl-3,5,7-tricarboxyadamantane, 1-acetyl-3-nitroadamantane, and 1,3-diacetyladamantane.

The compounds represented by the formula (8) to be used as materials in the acylation reaction can be prepared by a known technique. By way of illustration, an adamantane derivative having a hydroxyl group at a bridgehead position can be obtained by oxidizing an adamantane derivative having a hydrogen atom at a bridgehead position with oxygen in the presence of a catalyst composed of the imide compound represented by the formula (10), or a catalyst composed of the aforementioned catalyst and the metallic compound (C1). The amount of the imide compound is, for example, about 0.001 to 1 mole per mole of the adamantane derivative having a hydrogen atom at a bridgehead position; and the proportion of the metallic compound (C1) is, for instance, about 0.0001 to 0.7 mole per mole of the adamantane derivative having a hydrogen atom at a bridgehead position. The oxygen is generally used in excess moles to the adamantane derivative having a hydrogen atom at a bridgehead position. As the oxygen, molecular oxygen can be used. The reaction is carried out, for example, in a solvent such as acetic acid or another organic acid, or acetonitrile, benzonitrile, or another nitrile, at ambient pressure or under pressure at a temperature of about 0° C. to 300° C. (preferably 30° C. to 250° C.).

Likewise, an adamantane derivative having a carboxyl group at a bridgehead position can be obtained by allowing an adamantane derivative having a hydrogen atom at a bridgehead position to contact with carbon monoxide and oxygen, in the presence of a catalyst composed of the imide compound represented by the formula (10), or a catalyst composed of the aforementioned catalyst and the metallic compound (C1). The amounts of the imide compound and metallic compound (C1) are similar to those in the aforementioned oxidation reaction. The amount of carbon monoxide is, usually, equal to or more than 1 mole (e.g., 1 to 100 moles) per mole of the adamantane derivative having a hydrogen atom at a bridgehead position. The proportion of the oxygen is, for instance, equal to or more than 0.5 mole (e.g., 0.5 to 100 moles) per mole of the adamantane derivative having a hydrogen atom at a bridgehead position. The ratio of carbon monoxide to the oxygen is such that carbon monoxide:oxygen (by mole) equals about 1:99 to 99:1, preferably about 10:99 to 99:1. The reaction is carried out, for example, in a solvent such as acetic acid or another organic acid, or acetonitrile, benzonitrile, or another nitrile, at ambient pressure or under pressure at a temperature of about 0° C. to 200° C. (preferably 10° C. to 150° C.).

An adamantane derivative having a hydroxymethyl group at a bridgehead position can be obtained by reducing the above-mentioned adamantane derivative having a carboxyl group at a bridgehead position according to a conventional reduction process using a reducing agent (e.g., a hydrogen-platinum group metal catalyst, a sodium borohydride-Lewis acid, lithium aluminium hydride, or diborane).

An adamantane derivative having a nitro group at a bridgehead position can be obtained by allowing an adamantane derivative having a hydrogen atom at a bridgehead position to contact with a nitrogen oxide (e.g., $N_2O_3$, $N_2O$—$O_2$, NO—$O_2$, $NO_2$) in the presence of, or in the absence of, a catalyst composed of the imide compound represented by the formula (10). The amount of the imide compound is similar to that in the oxidation reaction. The proportion of the nitrogen oxide is generally about 1 to 50 moles, and preferably about 1.5 to 30 moles per mole of the adamantane derivative having a hydrogen atom at a bridgehead position. The reaction is performed, for example, in a solvent such as acetic acid or another organic acid, or acetonitrile, benzonitrile or another nitrile, at atmospheric pressure or under pressure at a temperature of about 0° C. to 150° C. (preferably 10° C. to 125° C.).

By reducing the aforementioned adamantane derivative having a nitro group at a bridgehead position according to a conventional reduction process using a reducing agent [e.g., a hydrogen-metal catalyst (e.g., a platinum group metal, nickel, or copper chromite), sodium borohydride, or diborane], an adamantane derivative having an amino group at a bridgehead position can be obtained. Compounds containing an acyl group, of the compounds of the formula (8), can be prepared by the use of an acylation process using the acylating agent.

Compounds where $R^x$ is a methyl group (1-acetyladamantane derivatives) among compounds of the formula (3) can also be obtained by reacting a 1-carboxyadamantane derivative represented by the following formula (11):

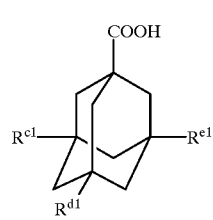

(11)

(wherein $R^{c1}$, $R^{d1}$ and $R^{e1}$ have the same meanings as defined above) with thionyl chloride or another halogenating agent to give a corresponding carboxylic acid halide derivative, and allowing a Grignard reagent derived from ethyl malonate or another malonic ester to act on the obtained carboxylic acid halide to give a corresponding α-(adamantylcarbonyl) malonic ester, and subsequently decomposing this compound with sulfuric acid or another acid.

In the compounds represented by the formulae (1), (3) and (8) [as well as in the compounds represented by the formulae (1b), (11), (12a) and (12b) as mentioned later], introduction and deprotection of protective groups can be performed according to a conventional technique. The above introduction techniques of individual functional groups (hydroxyl group, carboxyl group, hydroxymethyl group, nitro group, amino group and acyl group) can be applied to the preparation of material compounds in additional production processes for adamantanemethanol derivatives described below, and can be performed at any step of the production of the inventive adamantanemethanol derivatives.

Additional Production Processes for the Adamantanemethanol Derivatives

Among the adamantanemethanol derivatives represented by the formula (1), compounds where $R^a$ and $R^b$ are the same hydrocarbon group, i.e., compounds represented by the following formula (1a):

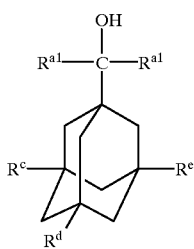

(1a)

(wherein $R^{a1}$ is a hydrocarbon group having a carbon atom, to which carbon atom at least one hydrogen atom is bonded, at a bonding site with the adjacent carbon atom, and the two substituents $R^{a1}$ are the same group; and $R^c$, $R^d$ and $R^e$ have the same meanings as defined above; where the other carbon atoms of carbon atoms constituting the adamantane skeleton than those at the bridgehead positions may each have a substituent) can also be obtained by reacting a 1-adamantanecarboxylic acid derivative represented by the following formula (12)

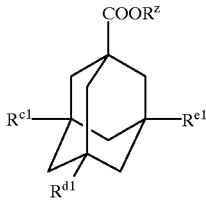

(12)

(wherein $R^z$ is a hydrogen atom or a hydrocarbon group which may have a substituent; and $R^{c1}$, $R^{d1}$ and $R^{e1}$ have the same meanings as defined above; where the other carbon atoms of carbon atoms constituting the adamantane skeleton than those at the bridgehead positions may each have a substituent) with an organometallic compound represented by the following formula (4a):

$$R^{a1}-M \quad (4a)$$

(wherein $R^{a1}$ and M have the same meanings as defined above).

Hydrocarbon groups in $R^{a1}$ in the formula (1a) include the hydrocarbon groups as exemplified in the substituent $R^b$. Preferred $R^{1a}$ includes, but is not limited to, $C_1$–$C_{10}$ alkyl groups (among them, $C_1$–$C_6$ alkyl groups, especially $C_1$–$C_4$ alkyl groups) and 3- to 8-membered cycloalkyl groups.

As hydrocarbon groups which may have a substituent in $R^z$ in the formula (12), there may be mentioned aliphatic hydrocarbon groups, alicyclic hydrocarbon groups, aromatic hydrocarbon groups and groups composed of a plurality of these groups bonded successively. The substituent includes, but is not limited to, halogen atoms, substituted oxy (or thio) groups (e.g., methoxy, methylthio, methoxyethoxy, 2-(trimethylsilyl)ethoxy, and benzyloxy groups), and acyl groups (e.g., benzoyl group).

The aliphatic hydrocarbon groups include, but are not limited to, methyl, ethyl, propyl, isopropyl, butyl, isobutyl, s-butyl, t-butyl, pentyl, hexyl, octyl, decyl, vinyl, allyl, 2-propynyl, and other $C_1$–$C_{10}$ aliphatic hydrocarbon groups (alkyl groups, alkenyl groups and alkynyl groups). Preferred aliphatic hydrocarbon groups are $C_1$–$C_6$ (especially $C_1$–$C_4$) aliphatic hydrocarbon groups. As the alicyclic hydrocarbon groups, there may be mentioned, for instance, cyclopentyl, cyclohexyl, and other 3- to 8-membered alicyclic hydrocarbon groups (cycloalkyl groups and cycloalkenyl groups). The aromatic hydrocarbon groups include, but are not limited to, phenyl, naphthyl, and other $C_6$–$C_{14}$ aromatic hydrocarbon groups. The groups composed of a plurality of different hydrocarbon groups bonded successively include, but are not limited to, benzyl, 2-phenylnaphthyl groups and other aralkyl groups each having about 7 to 16 carbon atoms.

Compounds where $R^z$ is a hydrocarbon group, of the compounds represented by the formula (12), can be prepared with facility from a 1-adamantanecarboxylic acid where $R^z$ is a hydrogen atom and a corresponding alcohol or phenol by, for example, a conventional esterification using an acid catalyst.

The reaction between the compound represented by the formula (12) and the organometallic compound represented by the formula (4a) is usually performed in an inert solvent. The solvent includes, but is not limited to, diethyl ether, dibutyl ether, 1,2-dimethoxyethane, tetrahydrofuran, and other chain or cyclic ethers; hexane, heptane, octane, and other aliphatic hydrocarbons; benzene, toluene, xylene, and other aromatic hydrocarbons; cyclohexane, and other alicyclic hydrocarbons; and mixtures of these solvents. Preferred solvents include the ethers or mixtures of the ethers with another solvent. The concentration of the ether in the solvent should preferably be equal to or more than 10% by weight.

The reaction temperature can freely be selected according to, for instance, the species of the organometallic compound, and generally ranges from about –100° C. to about 100° C. (in the case of an organo-magnesium compound, from about 0° C. to about 100° C., preferably from about 10° C. to about 40° C.). The amount of the organometallic compound represented by the formula (4a) can be chosen according to its species, and ranges, for example, from about 2- to about 4-fold equivalent (about 3- to 5-fold equivalent when $R^z$ in the formula (12) is a hydrogen atom) relative to the compound of the formula (12).

The reaction can be carried out in a batch system, semi-batch system, continuous system or another conventional system. When the reaction is performed in a semi-batch system, the compound of the formula (12) may be added (dropped) to a solution containing the organometallic compound of the formula (4a), or on the contrary, the organometallic compound of the formula (4a) may be added (dropped) to a solution containing the compound of the formula (12).

After the completion of the reaction, a corresponding α,α-di-substituted-1-adamantanemethanol derivative of the formula (1a) can be obtained by, usually, adding an aqueous solution containing an acid (e.g., hydrochloric acid, sulfuric acid or another inorganic acid; acetic acid or another organic acid) or a salt (e.g., ammonium chloride) to the reaction mixture to decompose adducts of the organometallic compound, adjusting the alkalinity or acidity of the mixture where necessary, and subjecting the mixture to a conventional separation and purification means. Such separation and purification means include filtration, concentration, extraction, distillation, crystallization, recrystallization, and column chromatography.

As the organometallic compound of the formula (4a), similar compounds as the compounds of the formula (4) can be employed.

If the compound of the formula (12) has a plurality of ester groups [$COOR^z$] in the molecule, an adamantanemethanol derivative having a plurality of groups represented by the formula (2a) can be obtained by selecting the reaction conditions (e.g., by adjusting the amount of the compound of the formula (4a)). In this case, a compound having different C-substituted hydroxymethyl groups (groups represented by the formula (2a)) in the molecule can also be obtained.

The inventive production process 2 utilizes the aforementioned technique. In the inventive production process 2, hydrocarbon groups which may have a substituent in $R^{z1}$ in the formula (12a) include similar groups as in the $R^z$. Introduction of a protective group into a hydroxyl group can be performed by a conventional reaction to introduce a protective group into a hydroxyl group (e.g., T. W. Greene, "Protective Group in Organic Synthesis", A Wiley-Interscience Publication, New York, 1981).

For instance, to protect a hydroxyl group of the compound of the formula (12a) by methoxymethyl, methylthiomethyl, 2-methoxyethoxymethyl, 2-(trimethylsilyl) ethoxymethyl or another substituted oxy- (or thio-)methyl group, the protective group can be introduced by reacting the compound of the formula (12a) with a substituted oxymethyl halide or the like (e.g., a substituted oxymethyl chloride, substituted oxymethyl bromide) corresponding to the substituted oxymethyl group or the like, preferably in the presence of a base such as triethylamine or pyridine. To introduce methyl group or another alkyl group as the protective group, the target protective group can be introduced by reacting the compound of the formula (12a) with an alkyl halide (e.g., an alkyl chloride, an alkyl bromide) corresponding to the alkyl group, preferably in the presence of the base. Likewise, to introduce acetyl group or another acyl group, an acyl halide (e.g., an acyl chloride or an acyl bromide) or another acylating agent corresponding to the acyl group should be subjected to the reaction. To introduce acetoacetyl group as the protective group, it can be introduced by reacting the compound of the formula (12a) with an acetoacetylating agent such as diketene or diketene-acetone adduct. In the introduction of a methyl group, diazomethane may be used.

Reaction conditions in the introduction of the protective group can freely be selected according to the type of the protective group. For example, the reaction temperature is about 0° C. to 150° C., and the amount of the reagent to be used in the introduction of the protective group is, for instance, about 0.8 to 3 moles relative to 1 mole of the compound of the formula (12a), and a large excess of the reagent may be used. The reaction is generally performed in an inert solvent.

The reaction product can be separated and purified by a conventional procedure such as filtration, concentration, adjustment of acidity or alkalinity, extraction, crystallization, recrystallization, distillation, or column chromatography.

In the formula (12b) thus obtained, hydrocarbon groups which may have a substituent in $R^{z2}$ include similar groups as in the $R^z$. If $R^{z1}$ in the formula (12a) is a hydrogen atom, it can be converted into a protective group [e.g., 2-methoxyethoxymethyl group or another substituted oxy- (or thio-)methyl group] in the reaction for introducing the protective group, depending on, for instance, the type, amount of the protective group or the reaction temperature.

The protective group for hydroxyl group represented by $R^p$ in the formula (12b) includes the aforementioned protective groups.

Hydrocarbon groups in $R^{a1}$ in the formula (4a) are the same as above. The reaction between the compound of the formula (12b) with the compound of the formula (4a) can be performed in the same manner as in the reaction between the compound of the formula (12) and the compound of the formula (4a). In this connection, compounds represented by the formula (1c) can be prepared by the use of compounds each having a plurality of ester groups [$COOR^{z1}$] as a material, among the compounds of the formula (12a). The compound represented by the formula (1b) can be separated and purified by any of the aforementioned conventional techniques.

The inventive production process 2 can yield, in a simple manner with efficiency, compounds of the adamantanemethanol derivatives represented by the formula (1), which compounds each have a hydroxyl group protected by a protective group at a bridgehead position of the adamantane ring, where $R^a$ and $R^b$ are the same hydrocarbon group.

The present invention provides novel adamantanemethanol derivatives each having a specific substituent on a carbon atom adjacent to the hydroxyl group.

According to the inventive production processes, the novel adamantanemethanol derivatives can be obtained by simple procedures in good yields.

EXAMPLES

The present invention will now be illustrated in more detail with reference to several examples below, which are not directed to limiting the scope of the invention.

Reference Example 1

A mixture of 0.3 mol of adamantane, 1.8 mol of biacetyl, 1.5 mmol of cobalt (II) acetate, and 300 ml of acetic acid was stirred at 60° C. under an oxygen atmosphere (1 atm) for 4 hours. The reaction mixture was concentrated to about 20% by weight, extracted with ethyl acetate, dried and washed with hexane to give 1-acetyladamantane in yield of 52% at a conversion rate from adamantane of 87%.

Reference Example 2

The procedure of Reference Example 1 was repeated, except that 0.3 mol of 1-adamantanol was used instead of adamantane, to give 1-acetyl-3-adamantanol in yield of 20% at a conversion rate from 1-adamantanol of 82%.

Spectrum data of 1-acetyl-3-adamantanol

IR (cm$^{-1}$): 3401, 2897, 2854, 1683, 1430, 1019, 605

$^{13}$C-NMR (CDCl$_3$)δ: 24.3, 29.9, 34.8, 36.8, 43.9, 45.4, 49.6, 67.9, 212.4

Example 1

A total of 1.1 mol of metallic magnesium was placed in a flask, the inner atmosphere of which was replaced with nitrogen, and a solution of 1.0 mol of 2-bromopropane in 500 ml of ethyl ether was put in the flask to an amount sufficient to dip the metallic magnesium. Next, a small portion of iodine was added to the mixture to start a reaction, and the residual etyl ether solution of 2-bromopropane was added dropwise at such a rate that the solvent was gently refluxed. After the completion of the addition, the reflux was continued for further 2 hours.

Separately, 1.0 mole of 1-acetyladamantane obtained according to the process described in Reference Example 1 was dissolved in 1000 ml of ethyl ether, and the resultant solution was added dropwise to the above reaction mixture at such a rate that the solvent was gently refluxed. After the completion of the addition, the reflux was continued for further 2 hours. The obtained reaction mixture was added dropwise gradually to a 10% hydrochloric acid (HCl: an amount corresponding to 1 mol) cooled on ice while stirring, and the mixture was further stirred at a temperature ranging from 0° C. to room temperature for 2 hours.

A 10% sodium hydroxide was added to the reaction mixture to adjust the mixture to around neutrality, and the mixture was separated to an organic layer and an aqueous layer; the aqueous layer was extracted with two portions of 1000 ml ethyl ether; the extract was added to the organic layer and concentrated; the concentrate was cooled for crystallization to give α-isopropyl-α-methyl-1-adamantanemethanol in yield of 46%.

Spectrum data of α-isopropyl-α-methyl-1-adamantanemethanol

MS m/e: 222 ([M$^{30}$ ]), 204, 189, 174, 159, 146

Example 2

The procedure of Example 1 was repeated, except that 1.0 mol of 1-acetyl-3-adamantanol obtained according to the process of Reference Example 2 was employed instead of 1-acetyladamantane, to give 3-hydroxy-α-isopropyl-α-methyl-1-adamantanemethanol in yield of 48%.

Spectrum data of 3-hydroxy-α-isopropyl-α-methyl-1-adamantanemethanol

MS m/e: 238 ([M$^{30}$]), 220, 202, 187, 172, 157, 144

Example 3

Initially, a 13% by weight ethylmagnesium bromide-tetrahydrofuran solution was prepared from ethyl bromide and metallic magnesium, and 61.51 g (0.060 mol) of the solution was placed in a flask. To this solution was added dropwise a solution of 4.76 g (0.02 mol) of n-butyl 1-adamantanecarboxylate in 7.21 g of tetrahydrofuran while maintaining the inner temperature not exceeding 35° C., followed by stirring at room temperature for 1 hour.

The obtained reaction mixture was added dropwise to 32.37 g of a 10% by weight sulfuric acid aqueous solution while maintaining the inner temperature not exceeding 35° C., and the resultant mixture was neutralized with a 5% by weight sodium hydroxide aqueous solution, and the neutralized mixture was separated. The obtained aqueous layer was extracted with two portions of 22.24 g of benzene, the extract was added to the organic layer, and the mixture was washed with a 22.24 g of a saturated sodium chloride aqueous solution, and was dried on anhydrous sodium sulfate. The dried product was filtered, and the filtrate was concentrated under reduced pressure to give α,α-diethyl-1-adamantanemethanol (purity: 48.8%). The yield on the basis of n-butyl 1-adamantanecarboxylate was 45.5%. α-Ethyl-1-adamantanemethanol, a reduction product of an intermediate, was by-produced (yield: 52%).

Spectrum data of α,α-diethyl-1-adamantanemethanol

GC-MS m/e: 204, 193, 175, 161, 147, 135, 86, 79, 67, 58, 41

Spectrum data of α-ethyl-1-adamantanemethanol

GC-MS m/e: 194 (M$_+$), 176, 165, 147, 135, 107, 93, 79, 67, 41

Example 4

A mixture of 5.07 mol of 1-adamantanecarboxylic acid, 507 mmol of N-hydroxyphthalimide, 5.07 mmol of cobalt (II) acetylacetonato and 12500 ml of acetic acid was stirred at 75° C. under an oxygen atmosphere (1 atm) for 8 hours. The reaction mixture was concentrated, and was subjected to column chromatography on a silica gel (eluent: chloroform/methanol (8/1)), and the obtained purified product was further recrystallized with ethanol/n-hexane to give 3-hydroxy-1-adamantanecarboxylic acid (yield: 38%) at a conversion rate from 1-adamantanecarboxylic acid of 99%.

Spectrum data of 3-hydroxy-1-adamantanecarboxylic acid

GC-MS m/e (FAB$^{31}$) : 195 (M-H)$^{-1}$H-NMR (500 MHz, DMSO-d$_6$) δ: 1.40–1.75(m, 12H), 2.11 (m, 2H), 11.97 (brs, 1H)

To 900 ml of toluene were added 300 mmol of the obtained 3-hydroxy-1-adamantanecarboxylic acid, 450 mmol of n-butanol, and 15 mmol of sulfuric acid, and the resultant mixture was stirred under reflux of toluene for 5 hours. The reaction mixture was concentrated and then subjected to column chromatography on a silica gel to give n-butyl 3-hydroxy-1-adamantanecarboxylate (yield: 94.1%). The conversion rate from 3-hydroxy-1-adamantanecarboxylic acid was 99%.

Spectrum data of n-butyl 3-hydroxy-1-adamantanecarboxylate

GC-MS m/e (FAB$^+$): 253 (M+H)$^+$

IR (cm-1): 3320, 2859, 1728, 1456, 1236

$^1$H-NMR (CDCl$_3$) δ: 0.7–2.8 (m, 22H), 4.3 (t, 2H)

A mixture of 200 mmol of n-butyl 3-hydroxy-1-adamantanecarboxylate, 220 mmol of 2-methoxyethoxymethyl chloride, 220 mmol of triethylamine and 200 ml of THF was refluxed for 3 hours. The reaction mixture was concentrated and subjected to column chromatography on a silica gel to give n-butyl 3-(2-methoxyethoxymethoxy)-1-adamantanecarboxylate (yield: 94.1%) at a conversion rate from n-butyl 3-hydroxy-1-adamantanecarboxylate of 99%.

Spectrum data of n-butyl 3-(2-methoxyethoxymethoxy)-1-adamantanecarboxylate

GC-MS m/e (FAB$^+$) : 341 (M+H)$^+$, 235, 89, 59

IR (cm$^{-1}$): 2932, 1728, 1455, 1121, 1100, 1082

¹H-NMR (500 MHz, CDCl₃) δ: 0.92 (t, 3H), 1.38 (dd, 2H), 1.50–2.02 (m, 16H), 2.22 (m, 2H), 3.38 (s, 3H), 1.38 (dd, 2H), 3.71 (t, 2H), 4.05 (t, 2H), 4.83 (s, 2H)

A total of 0.55 mol of metallic magnesium was placed in a flask and the inner atmosphere was replaced with nitrogen. Separately, 0.5 mol of bromomethane was dissolved in 250 ml of THF, and the resultant solution was put in the flask in such an amount as to dip the metallic magnesium. Next, a small portion of iodine was added to the mixture to start a reaction, and the rest of the THF solution of bromomethane was added dropwise to the mixture at such a rate that the solvent was gently refluxed. After the completion of addition, the reflux was continued for further 2 hours to give a methylamagnesium bromide solution.

A total of 100 mmol of n-butyl 3-(2-methoxyethoxymethoxy)-1-adamantanecarboxylate obtained according to the above process was dissolved in 150 ml of THF solution, and the resultant solution was added dropwise to the aforementioned methylmagnesium bromide solution at such a rate that the solvent was gently refluxed, and the reflux was continued for further 2 hours after the completion of addition. The obtained reaction mixture was added dropwise to a 10% by weight hydrochloric acid cooled on ice, while stirring, and the mixture was stirred at a temperature ranging from 0° C. to room temperature for further 2 hours. A 10% by weight sodium hydroxide aqueous solution was added to the reaction mixture to adjust the mixture to around neutrality, and the neutralized mixture was separated to an organic layer and an aqueous layer; the aqueous layer was extracted with toluene; the organic layer was concentrated; and the concentrate was subjected to column chromatography on a silica gel to give α,α-dimethyl-3-(2-methoxyethoxymethoxy)-1-adamantanemethanol in yield of 81% at a conversion rate from n-butyl 3-(2-methoxyethoxymethoxy)-1-adamantanecarboxylate of 90%.

Spectrum data of α,α-dimethyl-3-(2-methoxyethoxymethoxy)-1-adamantanemethanol

GC-MS m/e (FAB⁺): 299 (M+H)³⁰, 193, 89, 59

IR (cm⁻¹): 3380, 2928, 2912, 1119, 1102, 1078

¹H-NMR (500 MHz, CDCl₃) δ: 1.16(s, 6H), 1.4–2.0 (m, 13H), 2.22 (m, 2H), 3.38 (s, 3H), 3.56 (t, 2H),3.71 (t, 2H), 4.83 (s, 2H)

Example 5

A mixture of 1.92 mol of 1,3-adamantanedicarboxylic acid, 192 mmol of N-hydroxyphthalimide, 1.83 mmol of cobalt (II) acetylacetonato and 1290 ml of acetic acid was stirred at 80° C. under an oxygen atmosphere (1 atm) for 24 hours. The reaction mixture was concentrated and then separated by the addition of ethyl acetate and water. Sodium chloride was added to the aqueous layer and the layer was extracted with ethyl acetate; the organic layer was dried on anhydrous magnesium sulfate and was concentrated. The caked crude purified product was washed with ethyl acetate to give 5-hydroxy-1,3-adamantanedicarboxylic acid (yield: 52.5%) at a conversion rate from 1,3-adamantanedicarboxylic acid of 75%.

Spectrum data of 5-hydroxy-1,3-adamantanedicarboxylic acid

GC-MS m/e (FAB⁻): 239 (M–H)⁻ ¹H-NMR (500 MHz, DMSO-d₆)δ: 1.0–2.8(m, 13H), 12.2(brs, 1H)

To 900 ml of toluene were added 300 mmol of the obtained 5-hydroxy-1,3-adamantanedicarboxylic acid, 900 mmol of n-butanol and 30 mmol of sulfuric acid, and the resultant mixture was stirred under reflux of toluene for 5 hours. The reaction mixture was concentrated and subjected to column chromatogrpahy on a silica gel to give di-n-butyl 5-hydroxy-1,3-adamantanedicarboxylate in yield of 85.5% at a conversion rate from 5-hydroxy-1,3-adamantanedicarboxylic acid of 95%.

Spectrum data of di-n-butyl 5-hydroxy-1,3-adamantanedicarboxylate

GC-MS m/e: 353(M+H)⁺, 335, 150, 133, 57

A total of 1.375 mol of metallic magnesium was placed in a flask and the inner atmosphere was replaced with nitrogen. Separately, 1.25 mol of bromonethane was dissolved in 625 ml of THF, and the resultant solution was put in the flask in such an amount as to dip the metallic magnesium. Next, a small portion of iodine was added to the mixture to start a reaction, and the rest of the THF solution of bromomethane was added dropwise to the mixture at such a rate that the solvent was gently refluxed. After the completion of addition, the reflux was continued for further 2 hours to give a methylmagnesium bromide solution.

A total of 100 mmol of di-n-butyl 5-hydroxy-1,3-adamantanedicarboxylate obtained according to the above process was dissolved in 150 ml of THF solution, and the resultant solution was added dropwise to the above methylmagnesium bromide solution at such a rate that the solvent was gently refluxed. The reflux was continued for further 2 hours after the completion of addition. The obtained reaction mixture was added dropwise to a 10% by weight hydrochloric acid cooled on ice, while stirring, and the mixture was stirred at a temperature ranging from 0° C. to room temperature for further 2 hours. A 10% by weight sodium hydroxide aqueous solution was added to the reaction mixture to adjust the mixture to around neutrality, and the neutralized mixture was separated to an organic layer and an aqueous layer; the aqueous layer was extracted with n-butanol; the organic layer was concentrated; and the concentrate was subjected to column chromatography on a silica gel to give 5-hydroxy-α,α,α',α'-tetramethyl-1,3-adamantanedimethanol (yield: 81%) represented by the following formula. The conversion rate from di-n-butyl 5-hydroxy-1,3-adamantanedicarboxylate was 90%.

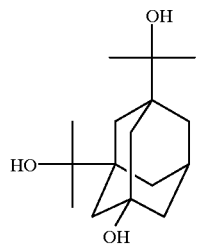

Spectrum data of 5-hydroxy-α,α,α',α'-tetramethyl-1,3-adamantanedimethanol

GC-MS m/e: 269, 209, 150, 133, 43

Example 6

A mixture of 200 mmol of di-n-butyl 5-hydroxy-1,3-adamantanedicarboxylate obtained in a similar manner to Example 5, 220 mmol of 2-methoxyethoxymethyl chloride, 220 mmol of triethylamine and 400 ml of THF was refluxed for 3 hours. The reaction mixture was concentrated and then subjected to column chromatography on a silica gel to give di-n-butyl 5-(2-methoxyethoxymethoxy)-1,3-adamkantanedicarboxylate in yield of 94.1% at a conversion rate from di-n-butyl 5-hydroxy-1,3-adamantanedicarboxylate of 99%.

Spectrum data of di-n-butyl 5-(2-methoxyethoxymethoxy)-1,3-adamantanedicarboxylate GC-MS m/e: 441 (M+H)[30], 335, 133, 89, 59

A total of 1.1 mol of metallic magnesium was placed in a flask and the inner atmosphere was replaced with nitrogen. Separately, 1.0 mol of bromomethane was dissolved in 500 ml of THF, and the resultant solution was put in the flask in such an amount as to dip the metallic magnesium. Next, a small portion of iodine was added to the mixture to start a reaction, and the rest of the THF solution of bromomethane was added dropwise to the mixture at such a rate that the solvent was gently refluxed. After the completion of addition, the reflux was continued for further 2 hours to give a methylmagnesium bromide solution.

A total of 100 mmol of the above-obtained di-n-butyl 5-(2-methoxyethoxymethoxy)-1,3-adamantanedicarboxylate was dissolved in 150 ml of THF solution, and the resultant solution was added dropwise to the above methylmagnesium bromide solution at such a rate that the solvent was gently refluxed. The reflux was continued for further 2 hours after the completion of addition. The obtained reaction mixture was added dropwise to a 10% by weight hydrochloric acid cooled on ice, while stirring, and the mixture was stirred for further 2 hours at a temperature ranging from 0° C. to room temperature. A 10by weight sodium hydroxide aqueous solution was added to the reaction mixture to adjust the mixture to around neutrality, and the neutralized mixture was separated to an organic layer and an aqueous layer; the aqueous layer was extracted with toluene; the organic layer was concentrated; and the concentrate was subjected to column chromatography on a silica gel to give 5-(2-methoxyethoxymethoxy)-α, α, α',α'-tetramethyl-1,3-adamantanedimethanol represented by the following formula in yield of 85.5%. The conversion rate form di-n-butyl 5-(2-methoxyethoxymethoxy)-1,3-adamantanedicarboxylate was 95%.

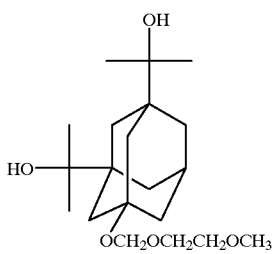

Spectrum data of 5-(2-methoxyethoxymethoxy)-α, α,α',α'-tetramethyl-1,3-adamantanedimethanol GC-MS m/e; 357(M+H)⁺, 251, 233, 215, 133, 89, 59

Example 7

A mixture of 5.07 mol of 1-adamantanecarboxylic acid, 507 mmol of N-hydroxyphthalimide, 5.07 mmol of vanadium (III) acetylacetonato and 12500 ml of acetic acid was stirred at 75° C. under blow of oxygen (1000 ml/min, 1 atm) for 24 hours. The reaction mixture was concentrated and then subjected to column chromatography on a silica gel (eluent: chloroform/methanol (3/1)), and the obtained purified product was further washed with acetone to give 3,5-dihydroxy-1-adamantanecarboxylic acid in yield of 24% at a conversion rate from 1-adamantanecarboxylic acid of 92%.

Spectrum data of 3,5-dihydroxy-1-adamantanecarboxylic acid $^1$H-NMR (500 MHz, DMSO-d$_6$) δ: 1.25–1.71(m,13 ), 4.62 (brs, 2H), 12.03 (brs, 1H)

$^{13}$C-NMR (500 MHz, DMSO-d$_6$) δ: 30.19, 36.70, 43.15, 44.27, 45.70, 52.46, 68.62, 177.13

A mixture of 0.14 mol of the obtained 3,5-dihydroxy-1-adamantanecarboxylic acid, 1.4 mol of n-butanol and 3.5 mmol of sulfuric acid was stirred at 100° C. for 8 hours. To the reaction mixture were added a saturated sodium chloride aqueous solution and a 5% sodium hydroxide aqueous solution (NaOH: 3.5 mmol), and the resultant mixture was subjected to separation. The organic layer was concentrated, and the concentrated residue was subjected to recrystallization from toluene to give n-butyl 3,5-dihydroxy-1-adamantanecarboxylate in yield of 86% at a conversion rate from 3,5-dihydroxy-1-adamantanecarboxylic acid of 99%.

Spectrum data of n-butyl 3,5-dihydroxy-1-adamantanecarboxylate $^1$H-NMR (500 MHz, DMSO-d$_6$) δ: 0.86(t, 3H), 1.32 (q, 2H), 1.37–1.62 (M, 14H), 2.19 (m, 1H), 3.99 (t, 2H), 4.56 (s, 2H)

A mixture of 120 mmol of n-butyl 3,5-dihydroxy-1-adamantanecarboxylate, 240 mmol of 2-methoxyethoxymethyl chloride, 240 mmol of diisopropylamine and 110 g of toluene was reacted at 80° C. for 3 hours. To the reaction mixture were added water and then a 5% sodium carbonate aqueous solution, and the resultant mixture was then separated. The organic layer was concentrated to give n-butyl 3,5-bis(2-methoxyethoxymethoxy)-1-adamantanecarboxylate (yield: 96%). The conversion rate of 3,5-bis(2-methoxyethoxymethoxy)-1-adamantanecarboxylate was 99.9%.

Spectrum data of n=butyl 3,5-bis(2-methoxyethoxymethoxy-1-adamantanecarboxylate $^1$H-NMR (500 MHz, CDCl$_3$) δ: 0.97 (t, 3H), 1.48 (dd, 2H), 1.60 (dd, 2H), 1.66–1.97 (m, 12H), 2.20(m, 1H), 3.39(s, 6H), 3.54 (t, 4H), 3.71 (t, 4H), 4.06 (q, 2H), 4.84 (s, 4H)

A total of 0.28 mol of metallic magnesium was placed in a flask and the inner atmosphere was replaced with nitrogen. Separately, 0.25 mol of bromomethane was dissolved in 157 g of THF, and the resultant solution was put in the flask in such an amount as to dip the metallic magnesium. Next, a small portion of iodine was added to the mixture to start a reaction, and the rest of the THF solution of bromomethane was added dropwise to the mixture at such a rate that the solvent was gently refluxed. After the completion of addition, the reflux was continued for further 2 hours to give a methylmagnesiunm bromide solution.

A total of 100 mmol of n-butyl 3,5-bis (2-methoxyethoxymethoxy)-1-adamantanecarboxylate obtained according to the above process was dissolved in 150 ml of THF solution, and the resultant solution was added dropwise to the above methylmagnesium bromide solution at such a rate that the solvent was gently refluxed. The reflux was continued for further 2 hours after the completion of addition. The obtained reaction mixture was added dropwise to a 10% by weight hydrochloric acid cooled on ice, while stirring, and the mixture was stirred for further 2 hours at a temperature ranging from 0° C. to room temperature. A 10% by weight sodium hydroxide aqueous solution was added to the reaction mixture to adjust the mixture to around neutrality, and the neutralized mixture was separated to an organic layer and an aqueous layer; the aqueous layer was extracted with toluene; the organic layer was concentrated; and the concentrate was subjected to column chromatogrpahy on a silica gel to give α, α-dimethyl-3,5-bis(2-methoxyethoxymethoxy)-1-adamantanemethanol (yield: 87%. The conversion rate from n-butyl 3,5-bis(2-methoxyethoxymethoxy)-1-adamantanecarboxylate was 98%.

Spectrum data of α,α-dimethyl-3,5-bis (2-methoxyethoxymethoxy)-1-adamantanemethanol $^1$H-NMR (500 MHz, CDCl$_3$)δ: 1.17 (s, 6H), 1.40–1.95 (m, 13H), 2.38 (m, 1H), 3.38 (s, 6H), 3.53–3.57 (m, 4H), 3.69–3.74 (m, 4H), 4.85 (s, 4H)

In this connection, 3,5-dihydroxy-α,α-dimethyl-1-adamantanemethanol can be obtained by reacting n-butyl 3,5-dihydroxy-1-adamantanecarboxylate obtained in the above intermediate step with methylmagnesium bromide according to the process described in Example 5.

What is claimed is:

1. An adamantanemethanol derivative represented by the following formula (1):

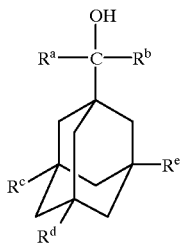

(1c)

wherein $R^a$ is a hydrogen atom or a hydrocarbon group; $R^b$ is a hydrocarbon group having a carbon atom, to said carbon atom at least one hydrogen atom being bonded, at a bonding site with the adjacent carbon atom; $R^c$, $R^d$ and $R^e$ are each, identical to or different from each other, a hydrogen atom, a halogen atom, an alkyl group, a hydroxyl group optionally protected by a protective a group, a hydroxymethyl group optionally protected by a protective group, an amino group optionally protected by a protective group, a carboxyl group optionally protected by a protective group, a nitro group, an acyl group, or a group represented by the following formula (2):

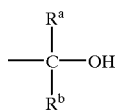

(2)

(wherein $R^a$ and $R^b$ have the same meanings as defined above); where the other carbon atoms of carbon atoms constituting the adamantane skeleton than those at the bridgehead positions are unsubstituted or have a substituent selected from the group consisting of oxo group, alkyl groups, acyl groups, hydroxyl group optionally protected by a protective group, carboxyl group optionally protected by a protective group, amino group optionally protected by a protective group, halogen atoms and cyano group; provided that (a) at least one of $R^c$, $R^d$ and $R^e$ is (i) a hydroxyl group protected by a protective group that can form an acetal group or hemi-acetal group with the hydroxyl group, an acyl group, a $C_1$–$C_4$ alkoxy-carbonyl group, a carbamoyl group, a substituted silyl group selected from the group consisting of trimethylsilyl group, t-butyldimethylsilyl group, tribenzylsilyl group and triphenylsilyl group, or a divalent hydrocarbon group, (ii) a hydroxymethyl group optionally protected by a protective group, (iii) an amino group optionally protected by a protective group, (iv) a carboxyl group, or (v) an acyl group, (b) $R^c$ is a group represented by the formula (2) provided that $R^d$ and $R^e$ are not concurrently hydrogen atoms or (c) at least two of $R^c$, $R^d$ and $R^e$ are hydroxyl groups.

2. An adamantanemethanol derivative according to claim 1, wherein $R^b$ is a hydrocarbon group having a methane carbon atom at a bonding site with the adjacent carbon atom.

3. An adamantanemethanol derivative according to claim 1, wherein $R^a$ and $R^b$ are each, identical to or different from each other, a $C_2$–$C_{10}$ alkyl group or a 3- to 8-membered cycloalkyl group.

4. An adamantanemethanol derivative according to claim 1, wherein $R^a$ and $R^b$ are the same hydrocarbon group.

5. An adamantanemethanol derivative according to claim 1, wherein a hydroxyl group protected by a protective group is bonded to at least one carbon atom constituting the adamantane skeleton.

6. An adamantanemethanol derivative of claim 1, wherein $R^a$ is a $C_1$–$C_6$ alkyl group or a 3- to 8-membered cycloalkyl group and $R^b$ is a $C_3$–$C_6$ alkyl group or a 3-to 8-membered cycloalkyl group having a methane carbon atom at a bonding site with the adjacent carbon atom.

7. An adamantanemethanol derivative of claim 1, wherein at least one of $R^c$, $R^d$ and $R^e$ is a hydroxyl group protected by a protective group that can form an acetal group or hemi-acetal group with the hydroxyl group, an acyl group, a $C_1$–$C_4$ alkoxy-carbonlyl group, a carbamoyl group, a substituted silyl group selected from the group consisting of trimethylsilyl group, t-butyldimethylsilyl group, tribenzylsilyl group and triphenylsilyl group, or a divalent hydrocarbon group.

8. An adamantanemethanol derivative of claim 1, wherein at least one of $R^c$, $R^d$ and $R^e$ is a hydroxyl group protected by a group that can form an acetal group or hemi-acetal group with the hydroxyl group or by a substituted silyl group selected from the group consisting of trimethylsilyl group, t-butyldimethylsilyl group, tribenzylsily group and triphenylsilyl group.

9. An adamantanemethanol derivative of claim 1, wherein $R^c$ is a group of formula (2) and $R^d$ is a hydroxyl group optionally protected by a protective group.

10. α,α-dimethyl-3-(2-methoxyethoxymethoxy)-1adamantanemethanol.

11. 5-hydroxy-α,α,α',α'-tetramethyl-1,3-adamantanedimethanol.

12. 5-(2-methoxyethoxymeethoxy)-α,α,α',α'-tetramethyl-1,3-adamantanedimethanol.

13. α,α-dimethyl-3,5-bis(2-methoxyethoxymethoxy)-1-adamantanemethanol.

* * * * *